(12) United States Patent
Pilauri et al.

(10) Patent No.: US 7,229,766 B2
(45) Date of Patent: *Jun. 12, 2007

(54) M-GAL: A GAL GENE SWITCH-BASED SUITE OF METHODS PROTEIN ANALYSES AND PROTEIN EXPRESSION IN MULTICELLULAR ORGANISMS AND CELLS THEREFROM

(75) Inventors: Vepkhia Pilauri, Hershey, PA (US); James E. Hopper, Hershey, PA (US); Gang Peng, Hershey, PA (US); Tamara Vyshkina, Elizabethtown, PA (US)

(73) Assignee: The Penn State Research Foundation, University Park, PA (US)

( * ) Notice: Subject to any disclaimer, the term of this patent is extended or adjusted under 35 U.S.C. 154(b) by 308 days.

This patent is subject to a terminal disclaimer.

(21) Appl. No.: 10/600,389

(22) Filed: Jun. 20, 2003

(65) Prior Publication Data

US 2004/0058368 A1    Mar. 25, 2004

Related U.S. Application Data

(60) Provisional application No. 60/390,872, filed on Jun. 20, 2002.

(51) Int. Cl.
*C12N 1/68* (2006.01)
*C12N 15/63* (2006.01)
*C07H 21/04* (2006.01)
*C12N 1/00* (2006.01)

(52) U.S. Cl. .................... 435/6; 435/320.1; 536/23.4

(58) Field of Classification Search .................... None
See application file for complete search history.

(56) References Cited

U.S. PATENT DOCUMENTS 5,283,173 A    2/1994  Fields et al.
6,878,524 B2 *  4/2005  Peng et al. ................... 435/7.1

OTHER PUBLICATIONS

Alarcon and Heitman, 1997, *Mol. Cell Bio.*, 17: 5968-5975.
Biggar and Crabtree 2001, *Embo. J.* 20:3167-3176.
Blank et al. 1997, *Mol Cell Biol.* 17: 2566-75.
Boder, ET, et al., *Methods in Enzymology* 1999 328: 430-443.
Brand AH, et al., *Development*. Jun. 1993; 118(2): 401-15.
Braunstein et al., 1993, *Genes Dev.* 7: 592-604.
Brown R, et al., *Enzyme Microb Technol.* Jun. 1, 2000; 26 (9-10): 801-807.
Buchert M, et al., *Biotechniques*. Sep. 1997; 23(3): 396-8, 400, 402.
Buckholz and Adams, 1981, *Molec. Gen. Genet.* 182: 77-81.
Cardenas et al., 1995, *Embo J* 14: 2772-2783.
Chen, S, et al., *Protein Expr Purif.* Dec. 1999; 17(3): 414-20.
Cook JC, et al., *Protein Expr Purif.* Dec. 1999; 17(3): 477-84.
Cormack et al., 1996, *Gene* 173: 33-38.
Dundr, M., et al., 2000 *J Cell Biol* 150 p433-446.
Feng, Xin-Hua, et al., *Two-Hybrid Systems* 2001 177: 222-239.
Ferreira BS, et al., *Appl Microbiol Biotechnol*. Mar. 2003; 61(1): 69-76.
Freshney, 1987, *Culture of Animal Cells*: pp. 89-104.
Frohman, *PCR Protocols: A Guide to Methods and Applications* 1990, pp. 228-236.
Fujiki and Verner, 1993, *J. Biol. Chem.* 268: 1914-20.
Funfschilling et al., 1999, *Mol. Biol. Cell*. 10: 3289-99.
Gerik KJ, et al., *J Biol Chem*. Jan. 10, 1997; 272(2): 1256-62.
Gillen et al., 1992, *J. Cell. Sci.* 111: 3235-44.
Griffith et al., 1995, *Cell* 82: 507-522.
Guldener et al., 1996, *Nucleic Acids Research* 24: 2519-2524.
Hansen MK, et al., *Receptors Channels*. 1999; 6(4): 271-81.
Hayden MS, et al., *Protein Expr Purif.* Mar. 1998; 12(2): 173-84.
Higuchi, *PCR Protocols: A Guide to Methods ad Application* 1990, pp. 177-183.
Hinz W, et al., *FEBS Lett*. Apr. 1, 1999; 448(1): 57-61.
Horikoshi M, et al., *Cell*. Aug. 26, 1988; 54(5): 665-9.
Hrdlicka L, et al., *Genesis*. Sep.-Oct. 2002; 34(1-2): 51-7).
Hwang WZ, et al., *J Agric Food Chem*. Oct. 2001; 49(10): 4662-6.
Innis, et al., *PCR Protocols: A Guide to Methods and Applications*—1990 pp. 3-27.
Jazwinsk, *Methods in Enzymology*—1990, 182:154-174.
Johnson et al., 1994, *Annu. Rev. Biochem*. 63: 869-914.
Johnston, M, 1987 *Microbiol. Rev.* 51:458-476).
Kino et al., 1987, *J Antibiot* (Tokyo) 40: 1249-1255.
Kokubo, et al., 1998, *Mol. Cell. Biol.* 189: 1003-1012.
Kuras et al. 1999, *Nature* 399: 609-613.
Lazo et al., 1977, *Eur. J. Biochem*. 77: 375-382.
Lee T, et al., *Trends Neurosci*. May 2001; 24(5): 251-4.
Liu et al., 1991, *Cell* 66: 807-815.
Lohr et al., 1987, *J. Biol. Chem.* 262: 15589-15597.
Luo Y, et al., *Biotechniques*. Feb. 1997; 22(2): 350-2).
McBride et al., 1992, *J. Cell. Biol* 119: 1451-1457.
Mitchell, DA, et al., 1993 *Yeast* 9: 715-723.
Mylin LM, et al., *Methods Enzymol*. 1990; 185:297-308.
Nogi,Y. and Fukasawa, T., *Molecular and Cellular Biology* 1989 9:3009-3017.
Panuwatsuk W, et al., *Biotechnol Bioeng*. Mar. 20, 2003; 81(6): 712-8.
Pang and Hopper, 2000, *Mol. Cell. Biol.* 20: 5140-5148.

(Continued)

*Primary Examiner*—Nancy Vogel
*Assistant Examiner*—Michele K. Joike
(74) *Attorney, Agent, or Firm*—McDonnell Boehnen Hulbert & Berghoff LLP

(57) ABSTRACT

The invention provides methods for detecting and analyzing protein-protein interactions and agonists and antagonists thereof, detecting and analyzing protein sequences, and regulatable gene expression in multicellular organisms or cells therefrom.

18 Claims, 9 Drawing Sheets

OTHER PUBLICATIONS

Post-Beittenmiller et al., 1984, *Molec. Cell. Biol.* 4: 1238-1245.
Resh et al., 1999, *Biochem. Biophys. Acta.* 1451: 1-16.
Rojo-Niersbach E, et al., *Biochem J.* Jun. 15, 2000; 348 Pt 3: 585-90.
Romanos, MA, et al., *Yeast* 8: 423-488.
Sadowski I, *Anal Biochem.* Feb. 15, 1998; 256(2): 245-7.
Sadowski, I, *Genetic Engineering*, 1995 17:119-147.
Sambrook et al., 2001, *Molecular Cloning*: A Laboratory Manual, 3rd ed.
Schart, PCR Protocols: *A Guide to Method and Applications* 1990—pp. 84-91.
Scott K, et al., *Cell.* Mar. 9, 2001; 104(5): 661-73.
Shioda T, et al., *Proc Natl Acad Sci U S A.* May 9, 2000; 97(10): 5220-4.
Sikorski and Hieter, 1989, *Genetics* 122: 19-27.
Stoscheck *Methods in Enzymology* 1990, 182:50-83.
Torchia et al., 1984, *Mol. Cell Biol.* 4: 1521-1527.
Vidal et al., 1996, *Proc. Natl. Acad. Sci. USA* 93:10315-20.
Ward, 1990 *Nucleic Acids Research* 18: 5319.
Webster N, et al., *Cell.* Jan. 29, 1988, 52(2): 169-78.
Yevenes A, et al., *Biochimie.* Feb. 2000; 82(2): 123-7.
Cull, *Method in Enzymology* 1990—182:147-153.
Bradley, *Method in Enzymology* 1990—182:112-119.
Peng et al., "Gene activation by interaction of an inhibitor with a cytoplasmic signaling protein" *PNAS* 99(13)8548-8553 (Jun. 25, 2002).

* cited by examiner

A.

B.

C.

|  | pGP74 | pGP144 | pGP147 |
|---|---|---|---|
| Gal3p expression level | 100 | 50 | 20 |
| α-galactosidase activity | 100±13 | 86±10 | 52±4 |

A.

B.

SEQUENCE LISTING

<160> NUMBER OF SEQ ID NOS: 38

<210> SEQ ID NO 1
<211> LENGTH: 16
<212> TYPE: PRT
<213> ORGANISM: Artificial sequence
<220> FEATURE:
<223> OTHER INFORMATION: N-myristoylation signal

<400> SEQUENCE: 1

Met Gly Cys Thr Val Ser Thr Gln Thr Ile Gly Asp Glu Ser Asp Pro
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: N-myristoylation signal variant

<400> SEQUENCE: 2

Met Ala Cys Thr Val Ser Thr Gln Thr Ile Gly Asp Glu Ser Asp Pro
1               5                   10                  15

<210> SEQ ID NO 3
<211> LENGTH: 29
<212> TYPE: PRT
<213> ORGANISM: Artificial sequence
<220> FEATURE:
<223> OTHER INFORMATION: mitochondria outer membrane signal anchor

<400> SEQUENCE: 3

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr
            20                  25

<210> SEQ ID NO 4
<211> LENGTH: 28
<212> TYPE: DNA
<213> ORGANISM: Artificial
<220> FEATURE:
<223> OTHER INFORMATION: PCR primer

<400> SEQUENCE: 4
aataccgcgg atgaatacaa acgttcca                                          28

<210> SEQ ID NO 5
<211> LENGTH: 30
<212> TYPE: DNA
<213> ORGANISM: Artificial
<220> FEATURE:
<223> OTHER INFORMATION: PCR primer

<400> SEQUENCE: 5
aataggatcc gcttgttcgt acaaacaagt                                        30

<210> SEQ ID NO 6
<211> LENGTH: 16
<212> TYPE: PRT
<213> ORGANISM: Artificial
<220> FEATURE:
<223> OTHER INFORMATION: The protein sequence encoded by GANG49/50
      nucleotide sequence annealed and inserted at the SpeI/PstI site
      to generate a Myr-Gal3 construct.

<400> SEQUENCE: 6

Met Gly Cys Thr Val Ser Thr Gln Thr Ile Gly Asp Glu Ser Asp Pro
1               5                   10                  15

<210> SEQ ID NO 7
<211> LENGTH: 26
<212> TYPE: DNA
<213> ORGANISM: Artificial sequence
<220> FEATURE:
<223> OTHER INFORMATION: primer

<400> SEQUENCE: 7
aactgcaggt atgtctaaag gtgaag                                         26

<210> SEQ ID NO 8
<211> LENGTH: 59
<212> TYPE: DNA
<213> ORGANISM: Artificial sequence
<220> FEATURE:
<223> OTHER INFORMATION: primer

<400> SEQUENCE: 8
ctagtatggg gtgtacagtg agtacgcaaa caataggaga cgaaagtgat ccttctgca     59

<210> SEQ ID NO 9
<211> LENGTH: 51
<212> TYPE: DNA
<213> ORGANISM: Artificial sequence
<220> FEATURE:
<223> OTHER INFORMATION: primer

<400> SEQUENCE: 9
gaaggatcac tttcgtctcc tattgtttgc gtactcactg tacaccccat a             51

<210> SEQ ID NO 10
<211> LENGTH: 48
<212> TYPE: DNA
<213> ORGANISM: Artificial sequence
<220> FEATURE:
<223> OTHER INFORMATION: primer

<400> SEQUENCE: 10
ctagtatgaa gagcttcatt acaaggaaca agacagccat tttggcaa                 48

<210> SEQ ID NO 11
<211> LENGTH: 53
<212> TYPE: DNA
<213> ORGANISM: Artificial sequence
<220> FEATURE:
<223> OTHER INFORMATION: primer

<400> SEQUENCE: 11
ccgttgctgc tacaggtact gccatcggtg cctactatta ttacggtgct gca           53

<210> SEQ ID NO 12
<211> LENGTH: 51

```
<212> TYPE: DNA
<213> ORGANISM: Artificial sequence
<220> FEATURE:
<223> OTHER INFORMATION: primer

<400> SEQUENCE: 12
gcaacggttg ccaaaatggc tgtcttgttc cttgtaatga agctcttcat a         51

<210> SEQ ID NO 13
<211> LENGTH: 42
<212> TYPE: DNA
<213> ORGANISM: Artificial sequence
<220> FEATURE:
<223> OTHER INFORMATION: primer

<400> SEQUENCE: 13
gcaccgtaat aatagtaggc accgatggca gtacctgtag ca                   42

<210> SEQ ID NO 14
<211> LENGTH: 51
<212> TYPE: DNA
<213> ORGANISM: Artificial sequence
<220> FEATURE:
<223> OTHER INFORMATION: primer

<400> SEQUENCE: 14
cagttgggtg gtggtggtcg ttacccatac gacgtcccag actacgctgc a         51

<210> SEQ ID NO 15
<211> LENGTH: 51
<212> TYPE: DNA
<213> ORGANISM: Artificial sequence
<220> FEATURE:
<223> OTHER INFORMATION: primer

<400> SEQUENCE: 15
gcgtagtctg ggacgtcgta tgggtaacga ccaccaccac ccaactgtgc a         51

<210> SEQ ID NO 16
<211> LENGTH: 29
<212> TYPE: DNA
<213> ORGANISM: Artificial sequence
<220> FEATURE:
<223> OTHER INFORMATION: primer

<400> SEQUENCE: 16
aactgcagat ttgtacaatt catccatac                                  29

<210> SEQ ID NO 17
<211> LENGTH: 27
<212> TYPE: DNA
<213> ORGANISM: Artificial sequence
<220> FEATURE:
<223> OTHER INFORMATION: primer

<400> SEQUENCE: 17
catggcatta ccaccatata catatcc                                    27

<210> SEQ ID NO 18
<211> LENGTH: 26
<212> TYPE: DNA
<213> ORGANISM: Artificial sequence
<220> FEATURE:
<223> OTHER INFORMATION: primer

<400> SEQUENCE: 18
```

| | |
|---|---|
| gaaggtttgt ggggccaggt tactgc | 26 |

<210> SEQ ID NO 19
<211> LENGTH: 22
<212> TYPE: DNA
<213> ORGANISM: Artificial sequence
<220> FEATURE:
<223> OTHER INFORMATION: primer

<400> SEQUENCE: 19

| | |
|---|---|
| gtgcatttgg ccttcaatga gc | 22 |

<210> SEQ ID NO 20
<211> LENGTH: 25
<212> TYPE: DNA
<213> ORGANISM: Artificial sequence
<220> FEATURE:
<223> OTHER INFORMATION: primer

<400> SEQUENCE: 20

| | |
|---|---|
| aagtgatgtt cgacatacct gtaac | 25 |

<210> SEQ ID NO 21
<211> LENGTH: 36
<212> TYPE: DNA
<213> ORGANISM: Artificial sequence
<220> FEATURE:
<223> OTHER INFORMATION: primer

<400> SEQUENCE: 21

| | |
|---|---|
| cgttacccat acgacgtccc agactacgct ggttgg | 36 |

<210> SEQ ID NO 22
<211> LENGTH: 36
<212> TYPE: DNA
<213> ORGANISM: Artificial sequence
<220> FEATURE:
<223> OTHER INFORMATION: primer

<400> SEQUENCE: 22

| | |
|---|---|
| cgccaaccag cgtagtctgg gacgtcgtat gggtaa | 36 |

<210> SEQ ID NO 23
<211> LENGTH: 25
<212> TYPE: DNA
<213> ORGANISM: Artificial sequence
<220> FEATURE:
<223> OTHER INFORMATION: primer

<400> SEQUENCE: 23

| | |
|---|---|
| gatacttccc aattcgtctt cagag | 25 |

<210> SEQ ID NO 24
<211> LENGTH: 32
<212> TYPE: DNA
<213> ORGANISM: Artificial sequence
<220> FEATURE:
<223> OTHER INFORMATION: primer

<400> SEQUENCE: 24

| | |
|---|---|
| ctggaataga ctagttgtgt attacgatat ag | 32 |

<210> SEQ ID NO 25
<211> LENGTH: 37
<212> TYPE: DNA
<213> ORGANISM: Artificial sequence

```
<220> FEATURE:
<223> OTHER INFORMATION: primer

<400> SEQUENCE: 25
ccaatgcatg tatgagtaaa ggagaagaac ttttcac                              37

<210> SEQ ID NO 26
<211> LENGTH: 26
<212> TYPE: DNA
<213> ORGANISM: Artificial sequence
<220> FEATURE:
<223> OTHER INFORMATION: primer

<400> SEQUENCE: 26
tttgtattgc atgcggatcg gggatc                                          26

<210> SEQ ID NO 27
<211> LENGTH: 39
<212> TYPE: DNA
<213> ORGANISM: Artificial sequence
<220> FEATURE:
<223> OTHER INFORMATION: primer

<400> SEQUENCE: 27
acaagtaata atcgatcgtc tgaagtaatt gaaggtaac                            39

<210> SEQ ID NO 28
<211> LENGTH: 35
<212> TYPE: DNA
<213> ORGANISM: Artificial sequence
<220> FEATURE:
<223> OTHER INFORMATION: primer

<400> SEQUENCE: 28
tttgctttta atcgattgtt gaccttcaac aattc                                35

<210> SEQ ID NO 29
<211> LENGTH: 64
<212> TYPE: DNA
<213> ORGANISM: Artificial sequence
<220> FEATURE:
<223> OTHER INFORMATION: primer

<400> SEQUENCE: 29
ataaactcgt gaaagcttaa agtaaggcct ttcacctaaa ctcgagtcgt tagaacgcgg     60
ctac                                                                  64

<210> SEQ ID NO 30
<211> LENGTH: 66
<212> TYPE: DNA
<213> ORGANISM: Artificial sequence
<220> FEATURE:
<223> OTHER INFORMATION: primer

<400> SEQUENCE: 30
tcaattaagg ctcagatact taccataaac ataaataaaa agcagtcact atagggagac     60
cggcag                                                                66

<210> SEQ ID NO 31
<211> LENGTH: 43
<212> TYPE: DNA
<213> ORGANISM: Artificial sequence
<220> FEATURE:
<223> OTHER INFORMATION: primer
```

<400> SEQUENCE: 31
tttaactttt acgcatgcaa atgccaatgg atttccaacc tac          43

<210> SEQ ID NO 32
<211> LENGTH: 41
<212> TYPE: DNA
<213> ORGANISM: Artificial sequence
<220> FEATURE:
<223> OTHER INFORMATION: primer

<400> SEQUENCE: 32
ggtggattta ggcgcctaat tccaagtctt ttcaattgtt c            41

<210> SEQ ID NO 33
<211> LENGTH: 40
<212> TYPE: DNA
<213> ORGANISM: Artificial sequence
<220> FEATURE:
<223> OTHER INFORMATION: primer

<400> SEQUENCE: 33
caacgccagc atgctgtcga aagacttgaa ttcttcacgc              40

<210> SEQ ID NO 34
<211> LENGTH: 40
<212> TYPE: DNA
<213> ORGANISM: Artificial sequence
<220> FEATURE:
<223> OTHER INFORMATION: primer

<400> SEQUENCE: 34
gtgcttagat cgattacgtt tcattcaaac cttcagtccc              40

<210> SEQ ID NO 35
<211> LENGTH: 41
<212> TYPE: DNA
<213> ORGANISM: Artificial sequence
<220> FEATURE:
<223> OTHER INFORMATION: primer

<400> SEQUENCE: 35
aaaaaagtac agcatgcaaa tgtcctccaa tcttaccgaa g            41

<210> SEQ ID NO 36
<211> LENGTH: 41
<212> TYPE: DNA
<213> ORGANISM: Artificial sequence
<220> FEATURE:
<223> OTHER INFORMATION: primer

<400> SEQUENCE: 36
gatgcaccta atcgattttt agataacaaa gcagcgaatt g            41

<210> SEQ ID NO 37
<211> LENGTH: 28
<212> TYPE: DNA
<213> ORGANISM: Artificial
<220> FEATURE:
<223> OTHER INFORMATION: PCR primer

<400> SEQUENCE: 37
aataccgcgg atggactaca acaagaga                           28

<210> SEQ ID NO 38
<211> LENGTH: 30

-continued

```
<212> TYPE: DNA
<213> ORGANISM: Artificial
<220> FEATURE:
<223> OTHER INFORMATION: PCR primer

<400> SEQUENCE: 38
aataggatcc gctaaactat aatgcgagat                                    30
```

M-GAL: A GAL GENE SWITCH-BASED SUITE OF METHODS PROTEIN ANALYSES AND PROTEIN EXPRESSION IN MULTICELLULAR ORGANISMS AND CELLS THEREFROM

This application claims priority to U.S. provisional application Ser. No. 60/390,872 filed Jun. 20, 2002.

This application was supported by a grant from the National Institutes of Health, No. R01 GM27925-22. The government may have certain rights in this invention. All patents, published patent applications and other references cited in the specification are incorporated herein in their entirety.

BACKGROUND OF THE INVENTION

1. Field of the Invention

This invention relates to methods for regulatable gene expression, detection and analysis of protein sequences, and detection and analysis of protein-protein interactions and agonists and antagonists thereof in multicellular organisms or cells therefrom.

This invention relates to interactions between biological molecules, particularly proteins, and methods for detecting and quantifying such interactions. The invention is particularly related to detection of protein-protein interactions that occur in the cellular cytoplasm of a cell from a multicellular organism. The invention further provides methods for detecting nuclear export sequences and nuclear localization sequences. This invention also relates to methods of regulatable gene expression. More specifically, the invention provides methods for inducible production of proteins in multicellular organisms or cells therefrom, including protein production from exogenously introduced GAL gene promoters, with or without galactose as the inducing molecule.

2. Background of the Related Art

The Human Genome Project has recently determined the complete human genetic sequence. From studies on only a very small fraction of the genome (likely less than 0.1%), it appears that protein-protein interactions most often comprise key mechanistic features of biological processes. Protein-protein interactions thus provide potential targets for therapeutic intervention in many disease states as well as manipulation of gene expression for any desired purpose.

Methods for detecting and analyzing of protein-protein interactions, as well as methods for achieving regulatable gene expression and detection and analysis of protein sequences, have been the focus of work based on several different native biological processes in a simple eucaryote, the yeast *Saccharomyces cerevisiae*. Such methods, which have generally employed native biological processes in *S. cerevisiae*, thereby using the yeast cell as the cellular platform, are recognized in the art as being useful in the biotechnology field, due in part to *S. cerevisiae*'s genetic tractability and ease of biochemical and molecular manipulation. Thus, basic discoveries related to several native biological processes in *S. cerevisiae* have been exploited for detecting and analyzing protein-protein interactions and agonists and antagonists thereof, as well as methods of regulatable gene expression and detection and analysis of protein sequences in yeast cells.

An example of a system that has been exploited for detecting and analyzing protein-protein interactions and protein sequences and methods of regulatable gene expression in *S. cerevisiae* is the Gal3p-Gal80p-Gal4p gene switch, also known as the Y-GAL gene switch. The Y-GAL gene switch has been used in many biotechnology applications (U.S. Pat. No. 6,221,630 to Hopper; Mylin LM, et al., Methods Enzymol. 1990; 185:297–308; Cook J C, et al., Protein Expr Purif. December 1999; 17(3): 477–84; Ferreira B S, et al., Appl Microbiol Biotechnol. March 2003; 61(1): 69–76; Panuwatsuk W, et al., Biotechnol Bioeng. Mar. 20, 2003; 81(6): 712–8; Hwang W Z, et al., J Agric Food Chem. October 2001; 49(10): 4662–6; Brown R, et al., Enzyme Microb Technol. Jun. 1, 2000; 26 (9–10): 801–807; Yevenes A, et al., Biochimie. February 2000; 82(2): 123–7; Chen S, et al., Protein Expr Purif. December 1999; 17(3): 414–20; Hansen M K, et al., Receptors Channels. 1999; 6(4): 271–81; Hinz W, et al., FEBS Lett. Apr. 1, 1999; 448(1): 57–61; Hayden M S, et al., Protein Expr Purif. March 1998; 12(2): 173–84; Gerik K J, et al., J Biol Chem. Jan. 10, 1997; 272(2): 1256–62; Broder, E T, et al., Methods in Enzymology 1999 328: 430–443; Mitchell, D A, et al., 1993 Yeast 9: 715–723; Romanos, M A, et al., Yeast 8: 423–488). The Y-GAL gene switch is comprised of three proteins: i) a site-specific DNA binding transcriptional activator (Gal4p) that is tightly associated with its cognate DNA site (the $UAS_{GAL}$ site) in the promoter regions of galactose-regulatable genes; ii) Gal80p, a protein that binds tightly to the transcriptional activation domain of Gal4p (amino acids 768–881) and inhibits Gal4p's capacity to recruit general transcription factors and RNA polymerase in the absence of galactose; and iii) Gal3p, a protein that binds to Gal80p in the presence of galactose and relieves Gal4p from Gal80p inhibition. Accordingly, Gal4p-mediated target gene expression occurs only in the presence of galactose (Johnston, M, 1987 Microbiol. Rev. 51:458–476).

The Y-GAL gene switch is a widely used tool for galactose-regulatable high level amplified expression of heterologous proteins in yeast (Mylin L M, et al., Methods Enzymol. 1990; 185:297–308; Cook J C, et al., Protein Expr Purif. December 1999; 17(3): 477–84; Ferreira B S, et al., Appl Microbiol Biotechnol. March 2003; 61(1): 69–76; Panuwatsuk W, et al., Biotechnol Bioeng. Mar. 20, 2003; 81(6): 712–8; Hwang W Z, et al., J Agric Food Chem. October 2001; 49(10): 4662–6; Brown R, et al., Enzyme Microb Technol. Jun. 1, 2000; 26 (9–10): 801–807; Yevenes A, et al., Biochimie. February 2000; 82(2): 123–7, Chen S, et al., Protein Expr Purif. December 1999; 17(3): 414–20; Hansen M K, et al., Receptors Channels. 1999; 6(4): 271–81; Hinz W, et al., FEBS Lett. Apr. 1, 1999; 448(1): 57–61; Hayden M S, et al., Protein Expr Purif. March 1998; 12(2): 173–84; Gerik K J, et al., J Biol Chem. Jan. 10, 1997; 272(2): 1256–62; Broder, ET, et al., Methods in Enzymology 1999 328: 430–443; Mitchell, D A, et al., 1993 Yeast 9: 715–723; Romanos, M A, et al., Yeast 8: 423–488). More recently, some of the instant inventors developed methodologies capable of detecting and characterizing protein-protein interactions, nuclear export and nuclear import sequences and galactose-independent inducibility of Gal4p-mediated gene expression in yeast by exploiting particular principles of the Y-GAL gene switch (see co-owned and co-pending U.S. patent application Ser. No. 10/165,873, incorporated herein in its entirety).

The protein-protein interaction method of Y-GAL gene switch methodologies is referred to as the "80-Trap method" and differs significantly from classical two-hybrid methods that depend on an intra-nuclear location of both interacting proteins. Specifically, in the 80-Trap method, the protein-protein interaction occurs within the cytoplasm but is reported (detected) by gene activation in the nucleus. Other methods provided in the Y-GAL gene switch methodologies are useful for detecting and analyzing nuclear export and nuclear import sequences. Additional methods provide a galactose-independent method of inducing Gal4p-mediated target gene expression. This last method provides for Gal4p-mediated activation of desired target genes by use of any low molecular weight, cell-permeant molecule that is a known effector of protein-protein interaction.

The methods provided, using the Y-GAL gene switch, exploit the fact that Gal4p's activation of target genes is regulated by Gal80p, a protein that binds to the Gal4p transcriptional activation domain and prevents it from recruiting general transcription factors required for recruiting RNA polymerase to the Gal4p-regulatable target promoter. These methods additionally take advantage of either one or more of three heretofore unappreciated mechanistic features of the Y-GAL gene switch. These newly-recognized mechanistic features are that i) Gal3p need not enter the nucleus to form a complex with the Gal80 protein in the presence of galactose; ii) when Gal80p, a nuclear/cytoplasmic shuttling protein, shuttles out of the nucleus it binds to cytoplasmically-restricted Gal3p; and, iii) binding of Gal80p to Gal3p in the cytoplasm reduces the amount of Gal80p in the nucleus available to bind to $UAS_{GAL}$-associated Gal4p at the gene promoter and, as a consequence, Gal4p-mediated transcriptional activation of Gal4p-regulated genes is increased. Thus, galactose-triggered interaction of Gal80p and Gal3p in the cytoplasm traps Gal80p in the cytoplasm and reduces the concentration of Gal80p in the nucleus. Consequently, the amount of Gal80p bound to Gal4p decreases, which results in Gal4p-mediated gene activation.

Unlike in yeast, there are very few existing methods for detecting and analyzing protein-protein interactions and agonists and antagonists thereof or regulatable gene expression in multicellular organisms or cells therefrom. Moreover, existing methods suffer from serious limitations. For example, one method to activate promoters in multicellular organisms or cells therefrom utilizes the Gal4 protein, the $UAS_{GAL}$-specific transcriptional activator of yeast referred to above. However, Gal4p expression in multicellular organisms or cells therefrom causes constitutive activation of target promoters containing the $UAS_{GAL}$ site (Sadowski, I, Genetic Engineering, 1995 17:119–147; Horikoshi M, et al., Cell. Aug. 26, 1998; 54(5): 665–9; Webster N, et al., Cell. Jan. 29, 1998; 52(2): 169–78; Brand A H, et al., Development. June 1993; 118(2): 401–15; Scott K, et al., Cell. Mar. 9, 2001; 104(5): 661–73; Hrdlicka L, et al., Genesis. September–October 2002; 34(1–2): 51–7). A method to regulate Gal4p-mediated target gene expression in mammalian calls has been developed that takes advantage of the FLP recombinase target sequence (FRT) and recombination by the FLP recombinase. This method involves engineering into the same cells an FRT-associated GAL80 gene that can be excised by the FLP recombinase when the expression of the recombinase gene is induced by the heat shock promoter (Lee T, et al., Trends Neurosci. May 2001; 24(5): 251–4). This system has numerous significant problems, among them the heat shock method of induction and the extended persistence of the Gal80 protein, which can remain in the cells for as long as 48 hours after recombination excision of the GAL80 gene sequences.

Another existing method used in mammalian cells is the Gal4p-based two-hybrid system for analysis of protein-protein interactions (Sadowski I, Genetic Engineering, 1995 17: 119–147; Sadowski I, Anal Biochem. Feb. 15, 1998; 256(2): 245–7; Feng, Xin-Hua, et al., Two-Hybrid Systems 2001 177: 222–239. Humana Press, Edited by Paul N. MacDonald; Shioda T, et al., Proc Natl Acad Sci U S A. May 9, 2000; 97(10): 5220–4; Rojo-Niersbach E, et al., Biochem J. Jun. 15, 2000; 348 Pt 3: 585–90; Buchert M, et al., Biotechniques. September 1997; 23(3): 396–8, 400, 402; Luo Y, et al., Biotechniques. February 1997; 22(2): 350–2). One serious limitation of two-hybrid methods in multicellular organisms or cells therefrom is they are not applicable for a very large number of proteins including, but not limited to, most transcriptional activators, transcriptional repressors, RNA polymerase II components, components of the general (basal) transcription machinery, and proteins that are associated with chromatin or participate in chromatin remodeling. This limitation stems from the existing two-hybrid methods' detection of protein-protein interaction by activating reporter genes through either direct binding to the RNA polymerase or through binding to other proteins that in turn bind to an RNA polymerase subunit. Another serious limitation of existing methods is that they require that the relevant protein-protein interactions and the detection thereof take place in the nucleus at the reporter gene promoter. Thus, a protein that normally does not enter the nucleus is unlikely to participate in its normal protein interaction(s) if targeted to and sequestered in the nucleus. For example, post-translational modification (e.g., phosphorylation) of cytoplasmic proteins is often mediated by interaction with one or more cytoplasmically-confined proteins; this process is illustrated in many well-established membrane-based receptor signaling cascades wherein proteins are often tethered to membranes or in close proximity to membrane-associated proteins. Thus, direct targeting to the nucleus of a protein that normally would be post-translationally modified in the cytoplasm would prevent or severely hinder such modifications required for normal biological activity. Therefore, existing methods in the art requiring nuclear localization of both interacting proteins are not useful for detecting a significant fraction of protein-protein interactions that normally occur within the cell.

Given the limitations of existing analytical systems in multicellular organisms and cells therefrom, there is a need in the art for methods that provide a capacity to detect and analyze protein-protein interactions and agonists and antagonists thereof, detect and analyze protein sequences, and for regulatable gene expression in multicellular organisms or cells therefrom, including non-mammalian cells such as, for example, plant cells, particularly wherein such methods detect protein-protein interactions in the cytoplasm. Considering the highly regulated nature of most biologically-interesting genes studied to date and the fact that the estimated number of protein-coding sequences in the human genome will turn out to be only 25,000 to 30,000, it is important not to exclude a large fraction of genes from protein-protein interaction analyses, as occurs using the methods known in the art. In view of the large number of genetic sequences being determined, there is a need in the art for methods of identifying and characterizing the properties of the protein products encoded thereby in multicellular organisms (and cells thereof), including vertebrates, invertebrates and plants.

SUMMARY OF THE INVENTION

The invention provides methods for detecting and analyzing protein-protein interactions and agonists and antagonists thereof, detecting and analyzing protein sequences, and producing regulatable gene expression, as well as reagents for performing said methods.

In a first aspect, the invention provides a method of detecting protein-protein interactions in a host cell cytoplasm. The method provides a first fusion protein between a first protein or protein-binding fragment thereof and a transcription inhibitor that can partition or shuttle between the cell nucleus or cytoplasm, and a second fusion protein between a second protein or protein-binding fragment thereof and a cytoplasmic membrane localization factor, wherein transcription of a gene operably linked to a promoter that is sensitive to or regulated by said transcription inhibitor is detected when the first fusion protein binds to the second fusion protein. In certain embodiments, the first protein or protein-binding fragment, the second protein or protein-binding fragment, or both the first and second protein or protein-binding fragment is encoded by a cDNA, for example, coding for a known protein or protein binding fragment, or a member of a cDNA library, i.e., an unknown protein or protein binding fragment. In a preferred embodiment, the cytoplasmic membrane lo localization factor is a cell membrane myristoylation signal or a mitochondrial membrane localization signal. In certain embodiments, the myristoylation sequence can be MGCTVSTQTIGDESDP (SEQ ID NO:1) or multicellular species-specific homolog thereof. Similarly, in certain embodiments, the mitochondrial outer membrane targeting sequence can be the N-terminal sequence of Tom70/Mas70 protein, MKSFITRNK-TAILATVAATGTAIGAYYYY (SEQ ID NO:3), or multicellular species-specific homolog thereof.

The invention also provides a first recombinant expression construct encoding the first fusion protein and a second recombinant expression construct encoding the second fusion protein, as well as cells, preferably cells from a multicellular organism, and most preferably human cells, comprising the first recombinant expression construct, the second recombinant expression construct or both said first and second recombinant expression constructs. In certain embodiments, said cells from a multicellular organism also comprise a gene operably linked to (inter alia, transcribed from) a promoter, wherein transcription from the promoter is sensitive to or regulated by inhibition by the transcription inhibitor comprising the first fusion protein. The product of the gene operably linked to the promoter that is sensitive to or regulated by inhibition by the transcription inhibitor is optionally a detectable product. Similarly, the gene operably linked to a promoter that is sensitive to or regulated by said transcriptional inhibitor can be a selectable gene, wherein increased expression of said gene confers a growth advantage on the cell or distinguishes the cell in some detectable manner. When the operably-linked gene is a selectable gene, the methods of this embodiment can further comprise placing the host cell under selective growth conditions and detecting increased growth or survival of said cells under said selective growth conditions, wherein said protein-protein interaction is detected thereby.

In other related embodiments, the first protein or protein-binding fragment, second protein or protein-binding fragment, or both first and second protein or protein-binding fragment can be a transcriptional activator protein or one of a multiplicity of proteins that participate in protein-protein interactions to bring about transcriptional activation. The first protein or protein-binding fragment, second protein or protein-binding fragment, or both first and second protein or protein-binding fragment can also be detectable or produce detectable metabolites. In other embodiments, the gene operably linked to a promoter that is sensitive to or regulated by said transcriptional inhibitor can be a gene expressed from a GAL4 protein activatable promoter, optionally one of a multiplicity of promoters that contain a $UAS_{GAL}$ site, and the gene expressed from the GAL4 protein activatable promoter can be one of a multiplicity of genes that encode detectable proteins. In additional related embodiments, the transcription inhibitor can be Gal80p.

In a second aspect, the invention provides methods for isolating the first or second fusion proteins of the above embodiments, the method comprising the steps of detecting increased expression of the gene operably linked to a promoter that is sensitive to or regulated by said transcriptional inhibitor; and isolating said first or second fusion proteins. As above, the first fusion protein, second fusion protein, or both the first and second fusion proteins can be encoded by one or a plurality of members of a cDNA library.

In a third aspect, the invention provides methods for detecting protein-protein interactions in the cytoplasm of a cell of a multicellular organism, the methods comprising the steps of introducing into a cell from a multicellular organism a first recombinant expression construct encoding a first protein or protein-binding fragment thereof fused with the amino- or carboxyl-terminus of Gal80p; and introducing into the cell from a multicellular organism a second recombinant expression construct encoding a second protein or protein-binding fragment thereof fused to a cytoplasm localization sequence, wherein upon interaction of the first and second proteins in the cell cytoplasm, said Gal80p is localized to the cytoplasm, wherein transcription of a gene operably linked to a promoter that is sensitive to or regulated by said Gal80p is increased; and detecting said increased transcription of said gene, wherein said protein-protein interaction is detected thereby. As in other aspects of the invention, the first and/or second protein or protein-binding fragment, in this aspect of the invention encoded by the first and second recombinant expression constructs, can be encoded by a cDNA, for example, coding for a known protein or protein-binding fragment, or a member of a cDNA library, i.e., an unknown protein or protein-binding fragment.

In the above aspects of the invention, as well as any aspects herein related to protein-protein interactions, when the first or second protein or protein-binding fragment thereof is a known protein, it is termed the "bait." The bait can be fused to either the transcriptional inhibitor, in preferred embodiments Gal80 protein, or targeted to a membrane, for example, the cell plasma and vesicular membranes or the mitochondrial outer membrane, by fusion with multicellular organism-based or synthetic cell membrane targeting and anchoring sequences. The protein or protein-binding fragment being tested for protein-protein interactions with the known bait protein is termed the "prey." When the known bait is fused to the transcriptional inhibitor, e.g., Gal80p, the prey is targeted to one of the above-mentioned membranes. Similarly, the known bait can be targeted to one of the above-mentioned membranes, wherein the prey is fused to transcriptional inhibitor. Further, unknown proteins or protein-binding fragments can be used for fusion to the transcriptional inhibitor and for targeting to the above-mentioned membranes. In such embodiments, both fusions are technically prey; however, the present invention nevertheless enables detection of interactions between two such prey fusions. Interaction between the two fusion proteins traps the transcriptional inhibitor in the cytoplasm, which reduces the amount of transcriptional inhibitor available to suppress transcription of a coding sequence operably-connected to a promoter sensitive to or regulated by the transcriptional inhibitor. For example, interaction between a Gal80p fusion protein and membrane localization sequence-containing fusion protein traps the Gal80p in the cytoplasm. Consequently, less Gal80p is available to bind to any nuclear Gal4p transcription activation domains introduced or otherwise present in the cell from a multicellular organism, which, in turn, activates transcription from any GAL promoters in the nucleus, inducing the expression of GAL reporter genes.

In this third aspect, the invention also provides a first recombinant expression construct encoding the first fusion protein comprising the first protein or protein-binding fragment (known, i.e., bait, or unknown, i.e., prey, as described above) thereof fused to the Gal80 protein, and a second recombinant expression construct encoding the second fusion protein comprising the second protein or protein-binding fragment (known, i.e., bait, or unknown, i.e., prey, as described above) thereof targeted to either the cell plasma and vesicular membranes or the mitochondrial outer membrane by fusion with multicellular organism-based or synthetic cell membrane targeting and anchoring sequences or mitochondrial outer membrane targeting and anchoring sequences, respectively. In this aspect are also provided cells, most preferably cells from a multicellular organism, comprising the first recombinant expression construct, the second recombinant expression construct or both said first and second recombinant expression constructs.

Thus, the invention broadly provides methods for detecting protein-protein interactions through the introduction of a first and second recombinant expression constructs into a cell, most preferably a cell from a multicellular organism, and expression of the first and second fusion proteins therein. Expression of a second fusion protein that does not bind to the first fusion protein results in no increase in a gene operably linked to a promoter sensitive to or regulated by the transcription inhibitor comprising said first fusion protein. Expression of a second fusion protein that does bind to the first fusion protein results in an increase in expression of a gene, optionally a reporter gene whose gene product is detectable, operably linked to a promoter sensitive to or regulated by the transcription inhibitor comprising said first fusion protein, because said first fusion protein partitions preferably to the cytoplasm and thereby releases transcription inhibition of said gene. In certain embodiments, said first fusion protein comprises a particular protein species, i.e., a known protein or protein-binding fragment. In alternative embodiments, said first fusion protein comprises a plurality of members of a cDNA library of species, i.e., an unknown protein or protein-binding fragment, wherein the first fusion protein comprises a plurality of fusion proteins in which the transcription inhibitor protein (such as Gal80p) is fused to each of a plurality of members of said cDNA library in each species of fusion protein comprising said plurality. In a preferred embodiment, said cell is a cell from a multicellular organism.

This method permits screening for and characterization of protein interactions in ways not possible using existing conventional two-hybrid approaches. The method is advantageous for identifying protein interactions wherein one or both proteins is a transcriptional activator, transcriptional repressor, RNA polymerase II component, a component of the general (basal) transcription machinery, or one or more of the very large number of proteins identified as being associated with chromatin or involved in chromatin remodeling, including transcriptional repressors, and proteins requiring cytoplasmic modification for interaction, as well as any other protein species that can form a specific binding pair with another protein species in the cytoplasm of the cell. This method is also advantageous for identifying protein interactions where one or both proteins require residence in the cytoplasm for native activity. The capacity of the inventive methods for targeting prey to different cellular environments (for example, plasma and vesicular membrane, outer mitochondrial membrane, and outer nuclear membrane and endoplasmic reticular membranes) within the cell from a multicellular organism is particularly advantageous in assays for certain protein interactions, such as for any proteins that have portions protruding into the cytoplasm. Additionally, semi-quantitative results comparing interactions between different protein pairs may be performed using the methods of this invention. The method also takes advantage of a wide range of existing two-hybrid reporters known in the art; moreover, the method can be performed in reverse two-hybrid or selection mode when, for example, the gene whose transcription is stimulated upon binding of the protein or protein-binding fragments of interest encodes a cytostatic or cytotoxic gene product. Interaction of the proteins or protein-binding fragments is identifiable through the death or growth cessation of the cells from a multicellular organism.

The invention also provides methods and reagents for detecting the presence of nuclear export sequences or nuclear import/localization sequences. In a fourth aspect, the invention provides a method for detecting in a host cell cytoplasm a nuclear export sequence (NES). The method comprises the steps of introducing into the cell a recombinant expression construct encoding a protein or protein-binding fragment containing putative NES fused with the amino- or carboxyl-terminus of a transcription inhibitor; assaying the cell for expression of a gene operably linked to a promoter that is sensitive to or regulated by said transcriptional inhibitor; and detecting increased expression of said gene, optionally a detectable product, wherein a NES is detected thereby. Similar to previous aspects of the invention, the recombinant expression construct can comprise a cDNA or a member of a cDNA library. In related embodiments, the gene that is operably linked to a promoter that is sensitive to or regulated by said transcriptional inhibitor can be a selectable gene, wherein increased expression of said gene confers a growth advantage or disadvantage on the cell or detectably distinguishes the cell. In such embodiments, the method for detecting in a host cell cytoplasm a nuclear export sequence (NES) can optionally comprise subjecting the host cell to selective growth conditions; and detecting increased or decreased growth or survival of said cells under selective growth conditions; wherein said NES is detected thereby.

In a fifth aspect, the invention provides a method for isolating a nuclear export sequence (NES) comprising detecting increased expression of a gene operably linked to a promoter that is sensitive to or regulated by Gal80p in a cell comprising a recombinant expression construct encoding a protein or protein-binding fragment containing a putative NES fused with the amino- or carboxyl-terminus of Gal80p; and isolating said NES from the protein fused to Gal80p. The gene operably linked to a promoter that is sensitive to or regulated by Gal80p can be a gene expressed from a GAL4 protein activatable gene promoter and can optionally encode a detectable protein. Likewise, the gene operably linked to a promoter that is sensitive to or regulated by Gal80p can be a selectable gene, wherein increased expression of said gene confers a growth advantage or disadvantage on the cell or distinguishes the cell in some detectable manner. In some embodiments, the GAL4 activatable promoter can be one of a multiplicity of promoters that contain a $UAS_{GAL}$ site. The NES can comprises one or a plurality of members of a cDNA library, wherein the first fusion protein comprises a plurality of fusion proteins in which the transcription inhibitor protein (such as Gal80p) is fused to each of a plurality of members of said cDNA library in each species of fusion protein comprising said plurality, wherein certain of the members of the cDNA species comprise an NES.

When the gene operably linked to a promoter that is sensitive to or regulated by Gal80p is a selectable gene that confers a growth advantage or disadvantage on the cell, the methods of this aspect can further comprise subjecting the host cell to selective growth conditions, and detecting increased or decreased growth or survival of said cells under selective growth conditions, wherein said NES is detected thereby.

In another related embodiment, the invention provides a more general method for isolating a nuclear export sequence (NES). The method comprises the steps of detecting increased expression of a gene operably linked to a promoter that is sensitive to or regulated by transcriptional inhibition in a cell comprising a recombinant expression construct encoding a protein or protein-binding fragment containing a putative NES fused with the amino- or carboxyl-terminus of a transcription inhibitor that inhibits said promoter that is sensitive to or regulated by transcriptional inhibition; and isolating said recombinant expression construct comprising said NES from the cell.

In a sixth aspect, the invention provides a method for detecting nuclear export sequences (NES) in a cytoplasm of a cell from a multicellular organism. The method comprises the steps of introducing a gene expressing a protein or fragment thereof fused with the amino- or carboxyl-terminus of Gal80p; assaying the cell for expression of a gene operably linked to a promoter that is sensitive to or regulated by Gal80p; and detecting increased expression of said gene, wherein an NES is detected thereby. In certain embodiments, the recombinant expression construct comprises a cDNA or a member of a cDNA library, wherein the first fusion protein comprises a plurality of fusion proteins in which Gal80p is fused to each of a plurality of members of said cDNA library in each species of fusion protein comprising said plurality, wherein certain of the members of the cDNA species comprise an NES.

In a seventh aspect, the invention provides a method for detecting a nuclear localization sequence (NLS) in a host cell comprising the steps of introducing into the cell a recombinant expression construct encoding a protein or protein-binding fragment containing a putative NLS fused with the amino- or carboxyl-terminus of a transcription inhibitor; assaying the cell for expression of a gene operably linked to a promoter that is sensitive to or regulated by said transcriptional inhibitor; and detecting decreased expression of said gene, wherein an NLS is detected thereby. In certain embodiments of this aspect, the gene operably linked to a promoter that is sensitive to or regulated by said transcriptional inhibitor can encode a product that converts a non-toxic compound to a cytotoxic or cytostatic compound. The recombinant expression constructs of this aspect of the invention can comprise a cDNA or a member of a cDNA library, wherein the first fusion protein comprises a plurality of fusion proteins in which the transcription inhibitor protein (such as Gal80p) is fused to each of a plurality of members of said cDNA library in each species of fusion protein comprising said plurality, wherein certain of the members of the cDNA species comprise an NLS.

In the aspects of the invention that relate to NLS detection, any NLSs that are native to the transcriptional inhibitor can be deleted or mutated (i.e., rendered non-functional or of limited function) prior to fusion to putative NLS-containing proteins or protein-binding fragments. In such embodiments, basal-level expression of the gene operably linked to the promoter that is sensitive to or regulated by said transcriptional inhibitor can be greatly increased, thereby enhancing the signal of any non-native NLS introduced in the methods herein. Such an embodiment is particularly useful when the product of the gene operably linked to the promoter that is sensitive to or regulated by said transcriptional inhibitor encodes a product that can convert a non-toxic compound to a cytotoxic or cytostatic compound, or simply encodes a toxic or cytostatic product itself. The present of a NLS decreases the expression of a product that is cytotoxic or cytostatic, thus conferring a growth advantage on those cells that have had a functional NLS fused to the protein or protein-binding fragment.

In other embodiments of this aspect of the invention, expression of the gene operably linked to a promoter that is sensitive to or regulated by said transcriptional inhibitor can be inducible when the cell is contacted with an inducing agent. In certain embodiments, the transcriptional inhibitor is Gal80p and the inducing agent can be galactose.

In still other embodiments of this aspect of the invention, the gene operably linked to a promoter that is sensitive to or regulated by the transcriptional inhibitor to which a NLS is fused encodes a product that converts a non-toxic compound to a cytotoxic or cytostatic compound and wherein expression of the gene operably linked to a promoter that is sensitive to or regulated by said transcriptional inhibitor is inducible when the cell is contacted with an inducing agent, wherein decreased expression of the gene is detected by cell growth or survival when the cell is contacted with both the inducing agent and the cytotoxic or cytostatic compound.

In an eighth aspect, the invention provides a method for isolating a nuclear localization sequence (NLS). The method comprises the steps of detecting decreased expression of the gene operably linked to a promoter that is sensitive to or regulated by a transcriptional inhibitor and encoded by a recombinant expression construct encoding a NLS-containing protein or NLS-containing fragment thereof fused with the amino- or carboxyl-terminus of the transcription inhibitor; and isolating said recombinant expression construct comprising said NLS from the cell.

In a related ninth aspect, the invention provides a method for detecting a nuclear localization sequence (NLS) in a host cell comprising the steps of introducing into the cell a recombinant expression construct encoding a NLS-containing protein or NLS-containing fragment thereof fused with the amino- or carboxyl-terminus of Gal80p; assaying the cell for expression of a gene operably linked to a promoter that is sensitive to or regulated by Gal80p; and detecting decreased expression of said gene, wherein an NLS is detected thereby. In certain embodiments, one or more of the native Gal80p NLSs are deleted or mutated (i.e., rendered non-functional) prior to fusion to putative NLS-containing protein or protein-binding fragments. Further, in a native-NLS-free background, sequences that act as NLSs or NESs can increase the nuclearity (in the case of a sequence acting as a NLS) or cytoplasmicity (in the case of a sequence acting as a NES). As above, a NES results in increased expression of a gene operably linked to the promoter that is sensitive to or regulated by Gal80p, and a NLS results in decreased expression of the gene operably linked to the promoter that is sensitive to or regulated by Gal80p.

In a tenth aspect, the invention provides a galactose-independent method of activating GAL4 protein regulatable gene expression in multicellular organisms or cells therefrom. The method comprises the steps of introducing into a cell from a multicellular organism a gene expressing a first protein or fragment thereof fused with the amino- or carboxyl-terminus of Gal80p; introducing into said cell from a multicellular organism a gene expressing a second protein or fragment thereof fused to a membrane targeting sequence; and treating the cell from a multicellular organism with an inducing agent, wherein treatment mediates the cytoplasmic interaction of the first and second proteins, relieving Gal80p inhibition and permitting Gal4p activation of GAL4 protein regulatable promoters, wherein the promoters are fused to a heterologous gene. The Gal4p or a fragment thereof can be expressed from a chromosomal Gal4p gene or a heterologous Gal4p gene introduced into the multicellular organisms or cells therefrom. The membrane targeting sequences can be a multicellular organism-based or synthetic myristoylation sequence, mitochondrial outer membrane targeting sequence, or other membrane targeting/anchoring sequences. In certain embodiments, the myristoylation sequence can be MGCTVSTQTIGDESDP (SEQ ID NO:1) or multicellular species-specific homolog thereof. Similarly, in certain embodiments, the mitochondrial outer membrane targeting sequence can be the N-terminal sequence of Tom70/Mas70protein, MKSFITRNKTAILATVAATGTAIGAYYYY (SEQ ID NO:3) or multicellular species-specific homolog thereof.

In certain embodiments of this aspect of the invention, the first and/or second proteins can be any protein encoded by a cDNA. In certain embodiments, the first protein can be Fpri and the second protein can be Cnal. The induction agent can be any molecule that mediates the interaction of said first and second proteins, and in certain embodiments the induction agent can be FK506.

The GAL4 protein-regulatable genes can be expressed from $UAS_{GAL}$ containing promoters. More specifically, the GAL4 protein regulatable gene can be transcribed through any promoter under the control of $UAS_{GAL}$ sequences and the $UAS_{GAL}$-specific transcriptional activator sequences.

In an eleventh aspect, the invention provides methods for regulatable gene expression in multicellular organisms or cells therefrom comprising the steps of introducing a recombinant expression construct encoding Gal80p into a multicellular organism or cell therefrom, introducing a recombinant expression construct encoding Gal3p into the multicellular organism or cell therefrom, introducing a recombinant expression construct encoding Gal4p into the multicellular organism or cell therefrom, introducing a coding sequence operably linked to a promoter sensitive to or regulated by Gal3p/Gal4p/Gal80p, and treating the multicellular organism or cell therefrom with an inducing agent, wherein treatment mediates the cytoplasmic interaction of the Gal3p and Gal80p, relieving Gal80p inhibition and permitting Gal4p activation of the coding sequence operably linked to the promoter sensitive to or regulated by the Gal80p, Gal3p and Gal4p, wherein the promoters are fused to a heterologous gene. In certain embodiments, the inducing agent is galactose. In other embodiments, Gal4p or a fragment thereof is expressed from a heterologous Gal4p gene introduced into the multicellular organisms or cells therefrom. In still other embodiments, the coding sequence is operably linked to a promoter sensitive to or regulated by Gal3p, Gal4p and Gal80p are expressed from $UAS_{GAL}$-containing promoters.

In a twelfth aspect, the invention provides methods for regulatable gene expression in multicellular organisms or cells therefrom comprising the steps of introducing a recombinant expression construct encoding Gal80p into the cell from a multicellular organism, introducing a recombinant expression construct encoding Gal3p into said cell from a multicellular organism, introducing a recombinant expression construct encoding Gal4p or a fragment thereof fused to a transcription factor or DNA-binding portion thereof into said cell of a multicellular organism, wherein the transcription factor or DNA binding fragment thereof is a transcription factor from a multicellular organism, introducing a coding sequence operably linked to a promoter sensitive to or regulated by the transcription factor, and treating the cell from a multicellular organism with an inducing agent, wherein treatment mediates the cytoplasmic interaction of the Gal3p and Gal80p, relieving Gal80p inhibition of the Gal4p-transcription inhibitor fusion protein and permitting activation of the coding sequence operably linked to the promoter sensitive to or regulated by the transcription factor. In certain embodiments, the coding sequence operably linked to the promoter sensitive to or regulated by the transcription factor is an endogenous gene. In other embodiments, the promoter sensitive to or regulated by the transcription factor is an endogenous promoters. In still other embodiments, the promoters operably linked to a heterologous gene. In yet further embodiments, the promoter is linked to a reporter gene. In other embodiments, the inducing agent is galactose.

Specific preferred embodiments of the present invention will become evident from the following more detailed description of certain preferred embodiments and the claims.

BRIEF DESCRIPTION OF THE DRAWINGS

FIG. 1A illustrates localization of Gal3p fused to green fluorescence protein (GFP) as visualized by fluorescence microscopy. Cells of yeast strain Sc781 (gal3Δ gal1Δ) carrying the indicated low-copy expression plasmid were grown to mid-log phase in medium containing 2% glycerol and 3% lactic acid as carbon source and induced with 2% galactose for 3 hours before microscopic observation. Green fluorescent protein (GFP) is inserted at the C termini of each of wild-type Gal3p, myristoylated Gal3p (Myr-Gal3p) and mMyr-Gal3p. The vacuolar (yeast lysosomal) membrane is readily seen in cells expressing Myr-Gal3GFP. For mitochondrial-associated Gal3p, the GFP sequence is positioned between the signal anchor sequence and the Gal3p sequence. Yeast mitochondria form the typical reticulum structure under the experiment conditions used. FIG. 1B shows MEL1 induction in cells carrying Gal3p derivatives. The results were obtained after 6 hours of galactose induction and were normalized to results obtained from cells carrying wild type Gal3p. The α-galactosidase induction assay was carried out essentially as described (Peng and Hopper, 2000, *Mol. Cell. Biol.* 20: 5140–5148). FIG. 1C shows membrane-associated Gal3p that sequesters Gal80p to membranes. Cells of yeast Sc786 strain (gal80Δ gal3Δ gal1Δ) carrying a low-copy plasmid expressing Gal80-GFP together with wild type Gal3p, or Myr-Gal3p, or mMyr-Gal3p, as indicated, were observed as in FIG. 1A. The images in FIG. 1C illustrate that Gal80-GFP molecules interact with membrane-associated Gal3p in galactose.

FIG. 2A shows sequence differences between different Gal3p encoding plasmids. pGP74 encodes a wild-type Gal3p expressed from an ADH2 promoter (SEQ ID NO. 39 & 40). pGP144 encodes myristoylated Gal3p (Myr-Gal3p) expressed from an identical ADH2 promoter (SEQ ID NO. 41 & 42). pGP 147 encodes a wild-type Gal3p expressed from a modified ADH2 promoter containing a 50bp sequence insertion between the promoter sequence and the start codon of Gal3p (SEQ ID NO. 43 & 44). Numbers in the promoter region correspond to the distance from the start codon in the ADH2 gene FIG. 2B illustrates results showing that different Gal3p expression levels were conferred by different Gal3p-encoding plasmids. Protein extracts from cells grown in the absence of galactose and from cells grown for 6 hours in the presence of galactose were analyzed by Western blot. FIG. 2C shows MEL1 induction in cells carrying plasmids pGP74, pGP144 or pGP147. Cells carrying each of the respective plasmids were induced with 0.5% galactose for 6 hours and cellular extracts prepared. Aliquots of the cellular extracts were subjected to Western blot analyses as shown in FIG. 2B to provide estimates for Gal3p expression levels. The a-galactosidase induction assay was carried out essentially as described (Peng and Hopper, 2000, *Mol. Cell. Bid.* 20: 5 140–8). Both Gal3p expression levels and MEL1 induction results were normalized to those of cells carrying pGP74.

FIG. 3A shows Gal4p and Gal80p occupancy at $UAS_{GAL}$ sites in un-induced and induced cells. The results from two-fold dilution of the template DNA used for the PCR reactions demonstrated that the reaction was within the linear range. Fold enrichments are indicated (enrichment). FIG. 3B shows Gal80p and Gal3p association with the $UAS_{GAL}$ region evaluated before and after galactose induction. FIG. 3C illustrates quantitation of promoter occupancy by Gal4p, Gal80p and Gal3p in un-induced and induced cells. Values are means (±standard deviation) of at least five experiments carried out with two sets of independently prepared chromatin samples.

FIG. 4A illustrates a small molecule other than galactose can be used to induce Gal4p mediated Gal promoter-mediated expression. FIG. 4A illustrates FK506-dependent HIS3 reporter expression. Gal80-Fpr1 designates the Gal80-Fpr1p fusion. Myr-Cna1 designates the plasma membrane targeted Cna1p. Myr-Cmd1 is a plasma membrane-targeted calmodulin and is used as a control. The nutrient agar plates used here lacked histidine, tryptophan and uracil and contained 0.5% galactose/3% glycerol/2% lactic acid as carbon source. FK506 was used at 0.25 µg/mL where indicated. Identical results were obtained using nutrient agar lacking galactose (data not shown). FIG. 4B shows galactose-independent HIS3 reporter expression as a result of Gal80-Fpr1p and Myr-Hom3p interaction. The nutrient agar plate lacked histidine, tryptophan and uracil and contained 3% glycerol/2% lactic acid as carbon source. Galactose was used at 0.5% where indicated. The lack of tryptophan and uracil are required for selection and maintenance in yeast of the two plasmids Gal80-Fpr1p and Myr-Cna1p, and the lack of histidine is to provide a selective assay for the protein-protein interaction that activates the HIS3 reporter gene carried on a yeast chromosome.

DETAILED DESCRIPTION OF THE PREFERRED EMBODIMENTS

Figure 1:
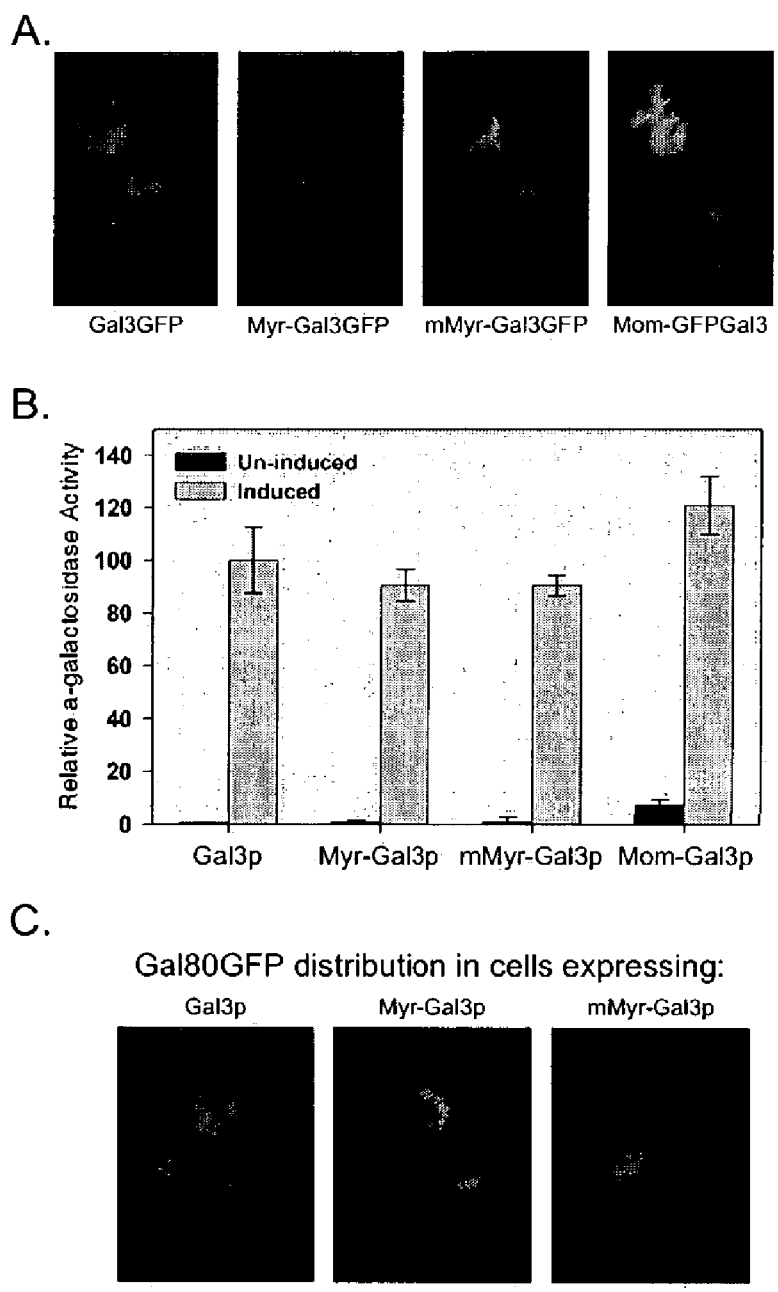
FIGS. 1A through 1C. (Yeast cells) Sequestration of Gal3p to cellular membranes does not affect its induction function. The results of assays performed as described in Example 1 establishes that Gal3p need not enter the yeast nucleus to mediate activation of Gal4p, and in turn, cause activation of Gal4p-activatable GAL gene promoters.

All references, patents and patent applications are hereby incorporated by reference in their entirety.

According to the teachings of this specification, unless otherwise stated, the techniques utilized may be found in any of several references known in the art, including but not limited to: *Molecular Cloning: A Laboratory Manual*, $3^{rd}$ ed. (Sambrook et al., 2001, Cold Spring Harbor Laboratory Press: New York); *Gene Expression Technology* (Methods in Enzymology, Vol. 185, Goeddel, ed., Academic Press, San Diego, Calif., 1991); "Guide to Protein Purification" in *Methods in Enzymology* (Deutshcer, ed., (1990) Academic Press, Inc.); *PCR Protocols: A Guide to Methods and Applications* (Innis et al., 1990, Academic Press, San Diego, Calif.); *Culture of Animal Cells: A Manual of Basic Technique*, $2^{nd}$ Ed. (Freshney, 1987, Liss, Inc. New York, N.Y.); *Gene Transfer and Expression Protocols*, pp. 109–128, Murray, ed., The Humana Press Inc., Clifton, N.J.), and the Promega 1996 Protocols and Applications Guide, $3^{rd}$ Ed. (Promega, Madison, Wis.).

This invention provides methods useful in multicellular organisms or cells therefrom for producing regulatable gene expression, detecting and analyzing protein sequences, and detecting and analyzing protein-protein interactions and agonists and antagonists thereof in multicellular organisms or cells therefrom. In particular, methods for detecting protein-protein interactions are provided that do not suffer from the limitations of existing methods used for multicellular organisms or cells therefrom referred to above.

The present invention provides methods based on previously unrecognized features and characteristics of the Gal3p-Gal80p-Gal4p gene switch of the yeast *Saccharomyces cerevisiae*. Specifically, prior to the instant invention it was unknown whether the yeast GAL gene switch could be used in multicellular organisms or cells therefrom to provide regulatable, in contrast to constitutive, gene expression. More specifically, it was not known in multicellular organisms or cells therefrom whether; i) Gal80p could shuttle between cytoplasm and the nucleus and, ii) Gal3p is restricted to the cytoplasm. These features are necessary for the "native" GAL switch to work in multicellular organisms or cells therefrom as it does in yeast. The realization that these two features of the GAL gene switch mechanism can be realized in multicellular organisms or cells therefrom is provided herein. As disclosed in more detail herein, Gal80p can shuttle between cytoplasm and the nucleus and Gal3p is restricted to the cytoplasm in cells from a multicellular organism. Thus, the Gal3p-Gal80p-Gal4p gene switch can be used in multicellular organisms or cells therefrom to provide methods for regulatable gene expression, detecting and analyzing protein sequences, and detecting and analyzing protein-protein interactions and agonists and antagonists thereof in multicellular organisms or cells therefrom. Also provided herein are Gal80-Trap-like systems utilizing other proteins to accomplish the same investigatory roles in multicellular organisms or cells therefrom.

As used herein, the plurality of methods provided by this invention are collectively termed M-GAL. The invention provides methods based on a GAL gene switch for detecting and analyzing protein-protein interactions, nuclear export and nuclear import sequences and galactose-independent and galactose-dependent inducibility of Gal4p-mediated gene expression in multicellular organisms or cells therefrom. M-GAL embodies some basic principles of the Y-GAL gene switch as described in co-owned and co-pending U.S. patent application Ser. No. 10/165,873. Thus, although the M-GAL methods are based on the Gal3p-Gal80p-Gal4p gene switch of yeast, M-GAL is a system based entirely in multicellular organisms or cells therefrom. M-GAL can comprise the Gal3p-Gal80p-Gal4p gene switch elements designed into a platform of multicellular organisms or cells therefrom, but, importantly, the M-GAL methods can be designed to operate analogously to native Y-GAL and thus comprise other proteins that serve the same biological purpose of the Gal3p-Gal80p-Gal4p gene switch proteins.

The present invention provides methods for detecting and analyzing protein-protein interactions and agonists and antagonists thereof, detecting and analyzing protein sequences, and regulatable gene expression in multicellular organisms or cells therefrom, as well as reagents for performing said methods in multicellular organisms or cells therefrom.

This invention is based, in part, on the discovery that Gal80p, which is an inhibitor of the transcriptional activator Gal4p, can be prevented from inhibiting Gal4p-mediated transcriptional activation of GAL gene promoters when Gal80p is preferentially sequestered or trapped in the cytoplasm. Gal80p binds with high affinity to a specific portion of the Gal4p transcriptional activation domain, and blocks Gal4p's ability to recruit RNA polymerase II at $UAS_{GAL}$ sites contained in GAL gene promoters. In native yeast, Gal80p binding within the Gal4p transcriptional activation domain is relieved by the interaction between Gal3p and Gal80p, an interaction that occurs only in the presence of galactose. Normally Gal80p shuttles dynamically between the yeast nucleus and cytoplasm, and under steady state conditions in the absence of galactose a sufficiently high concentration of Gal80p is in the nucleus to bind to Gal4p and keep Gal4p inactive and the GAL regulon transcriptionally silent. However, in the presence of galactose, Gal80p, binds to Gal3p molecules that are normally confined to the cytoplasm in native yeast cells, resulting in insufficient Gal80p in the nucleus to inhibit Gal4p. Consequently, Gal4p is able to activate genes of the galactose regulon, as well as reporter genes expressed via $UAS_{GAL}$ promoters. We discovered that the principles of the Gal80-Trap system could translate to other interacting proteins, i.e., proteins other than Gal80p and Gal3p. and, unexpectedly, that these systems could translate to more complex systems than yeast, namely multicellular organisms and cells therefrom. Thus, whenever the Gal80-Trap system is described herein, even when specifically describing, for example, Gal80p, Gal3p and galactose, the principles apply to analogous Gal80-Trap-like systems that comprise interacting proteins that correspond to the Gal80p transcriptional repressor, the Gal3p binding partner (or "second protein") and the galactose effector of protein-protein interactions, the actions of which can combine to influence the transcription of a promoter in the multicellular organisms-or cells therefrom. Preferably, the transcribed protein is detectable, thus enabling the indirect detection of protein-protein interactions.

To elaborate, the methods provided by this invention can be used with any transcriptional regulatory factors wherein the expression of a gene is mediated by a transcriptional activator that is in turn regulated by a nucleocytoplasmic transcriptional inhibitor. In the practice of the inventive methods, the known ("bait") or unknown ("prey") proteins or protein-binding fragments can be fused to any protein that functions as both a nucleocytoplasmic shuttling protein and an inhibitor or repressor of transcriptional activation. Localization of the transcriptional inhibitor/repressor in the nucleus prevents transcriptional activation by inhibiting the transcriptional activator, repressing recruitment of RNA polymerase, or other means. Conversely, localization of the transcriptional inhibitor in the cytoplasm permits transcriptional activator-mediated gene expression. Proteins or protein-binding fragments that interact with the protein or protein-binding fragment that is fused to the transcriptional inhibitor are targeted to the cytoplasm, preferably by fusion to a sequence specific for cytoplasmic localization, such as a multicellular organism-based or synthetic cytoplasmic membrane localization sequence. Protein-protein interactions between the bait and prey proteins results in an imbalance in the kinetics or stoichiometry of nuclear/cytoplasmic partitioning of the transcription inhibitor in favor of the cytoplasm, thereby releasing transcription inhibition and increasing transcription of genes regulated by promoters sensitive to the inhibitor. As described above, the present invention comprises bait-bait, prey-prey, prey-bait and bait-prey couplings, depending on whether the proteins or protein-binding fragments fused to the transcription inhibitor and membrane targeting sequence are known, i.e., bait or unknown, i.e., prey. In some embodiments, genes having increased transcription as a consequence of cytoplasmic localization of the transcription inhibitor are endogenous cellular genes or reporter genes operably linked to an endogenous or exogenous promoter sensitive to the inhibitor. In other related embodiments, genes having increased transcription as a consequence of cytoplasmic localization of the transcription inhibitor are exogenous cellular genes or reporter genes operably linked to an endogenous or exogenous promoter sensitive to the inhibitor. The promoter sensitivity is preferably mediated by the promoter being dependent on a transcription activator whose transcriptional activating activity is inhibited by the transcription inhibitor. The methods of the invention are provided to be used in the forward direction, i.e. detection of gene expression in the presence of protein-protein interactions, or the reverse direction, i.e. detection of loss of gene expression when said protein-protein interaction is inhibited or disrupted.

The invention provides a method for detecting protein-protein interactions in a host cell cytoplasm, the method comprising the steps of introducing into a cell a gene, or coding sequence (for example cDNA), expressing a first protein or protein-binding fragment thereof fused with the amino- or carboxyl-terminus of a transcriptional inhibitor; introducing into said cell a gene, or coding sequence (for example cDNA), expressing a second protein or protein-binding fragment thereof fused to a cytoplasm localization sequence, wherein upon interaction of the first and second proteins in the cell cytoplasm, said transcriptional inhibitor is preferentially localized to the cytoplasm, wherein transcription of a gene operably linked to a promoter that is sensitive to or regulated by said transcriptional inhibitor is increased; and wherein the protein-protein interaction is detected by detecting said increased transcription of said gene.

In preferred embodiments, the cytoplasm localization sequence is a membrane targeting sequence, preferably a multicellular organism-based or synthetic cell membrane targeting sequence or a mitochondrial membrane targeting sequence. Preferably, the cell is a cell from a multicellular organism. In certain embodiments, the gene, or coding sequence (for example cDNA), is operably linked to a promoter that is sensitive to or regulated by said transcriptional inhibitor and is an exogenous reporter gene, most preferably encoding a detectable product, such as a product that produces a detectable metabolite or detectable phenotype (e.g., a growth advantage or disadvantage).

As used herein, the term "gene" can comprise a native genetic sequence or other natural or synthetic, processed or unprocessed (i.e., a gene including exons and introns or a cDNA), coding or non-coding sequence.

As used herein, the term "operably linked" refers to components such as genetic components that are in a relationship, specifically covalently linked to one another, permitting them to function in their intended manner. For example, a control sequence "operably linked" to a protein coding sequence is ligated thereto so that expression of the protein coding sequence is achieved under conditions compatible with the transcriptional activity of the control sequences. In particular, a transcriptionally-regulated promoter is covalently linked in an orientation, typically 5' to an open reading frame encoding an amino acid sequence of a protein, such as a reporter gene or a fusion protein of the invention, so that transcription of the coding sequence is appropriately regulated.

As used herein, the terms "fused" and "fusion protein" are intended to mean that the sequences, such as the amino acid sequences of the protein, are covalently linked to one another. When used with regard to nucleic acids encoding a fusion protein, the term refers to covalent linkage of the sequences to be properly "in frame," so that translation of a mRNA encoding the fusion protein properly translates the individual components thereof in the proper reading frame of the genetic code.

As used herein, the term "protein binding fragments" is intended to encompass fragments of a protein involved in a protein-protein interaction that produces or is capable of producing a detectable signal according to the methods of the invention. Said fragments are capable of mediating the protein-protein interaction and are therefore necessary components of the fusion proteins of the invention. It will be recognized that other portions of the native protein involved in the protein-protein interactions assayed by the inventive methods may contribute to the interaction, but at least the portions termed "protein binding fragments" are required for the protein-protein interaction to take place.

As used herein, the term "bait" refers to a known protein or protein-binding fragment, or coding sequence therefor. Bait can be fused to a transcriptional inhibitor, for example Gal80p, or other sequences, for example multicellular organism-based or synthetic membrane targeting sequences. Herein, bait can bind to other known proteins or protein-binding fragments (i.e., other bait), or to unknown proteins or protein-binding fragments (i.e., prey). Thus, the present invention comprises bait-bait, bait-prey, prey-bait and prey-prey interactions.

As used herein, the term "prey" refers to an unknown protein or protein-binding fragment or coding sequence therefore. Prey can be fused to a transcriptional inhibitor, for example Gal80p, or other sequences, for example multicellular organism-based or synthetic membrane targeting sequences. Herein, prey can bind to other known proteins or protein-binding fragments (i.e., bait), or to other unknown proteins or protein-binding fragments (i.e., other prey). Thus, the present invention comprises bait-bait, bait-prey, prey-bait and prey-prey interactions.

In certain embodiments, the gene operably linked to a promoter that is sensitive to or regulated by the transcriptional inhibitor to which a protein or protein-binding fragment is fused is a selectable gene, wherein increased transcription of said selectable gene permits growth of the cell in selective conditions. In these embodiments, the inventive methods further comprise subjecting the host cell to selective growth conditions, and detecting increased growth or survival of said cells under selective growth conditions, wherein said protein-protein interaction is detected thereby.

In certain embodiments, a known (bait) or unknown (prey) protein or protein-binding fragment is fused to any native transcriptional inhibitor from a cell from a multicellular organism to create a fusion protein. Said fusion protein can also comprise additional sequences, for example, a myristoylation or mitochondrial outer membrane sequence from a multicellular organism. Alternatively, where a promoter that is responsive to the native Gal80-Trap system components is present in the cell from a multicellular organism (i.e., a $GAL_{UAS}$-sequence containing promoter is exogenously introduced or introduced using standard genetic techniques), and optionally operatively-coupled to a gene than encodes a protein whose transcription is detectable, Gal80p can serve as the transcriptional inhibitor to which a bait protein or protein binding fragment can be fused at either the Gal80p amino- or carboxyl-terminus. The binding partner of the above-mentioned known (bait) or unknown (prey) protein or protein-binding fragment fused to any native transcriptional inhibitor from a cell from a multicellular organism to create a fusion protein, is either another known protein or protein-binding fragment or unknown protein or protein-binding fragment, for example, one of a multiplicity of unidentified potential partners encoded in a cDNA library. This binding partner is tethered in the cytoplasm, particularly to a membrane via fusion to a membrane targeting sequences, for example, a multicellular organism-based or synthetic myristoylation sequence or one of a multiplicity of plasma membrane, vesicular membrane or mitochondrial outer membrane targeting sequences known in the art. If the bait-bait, bait-prey, prey-bait or prey-prey partners interact in the cytoplasm, the transcriptional inhibitor is preferentially partitioned or trapped in the cytoplasm and prevented from inhibiting transcriptional activation of its corresponding promoter(s) in the nucleus.

In additional embodiments, recombinant molecules are provided comprising the Gal4p transcription activation domain fused to the DNA-binding domain of other endogenous or exogenous DNA site-specific binding proteins. Using such constructs, reduced levels of Gal80p in the nucleus activate genes whose promoters contain the cognate binding site for the DNA-specific binding protein domain fused to the Gal4p transcription activation domain.

As described above, the methods and reagents of the invention are designed to allow bait and prey fusions in either direction, i.e., wherein the "bait" protein or specific binding fragment thereof is fused to the transcriptional repressor protein (e.g., Gal80p) and the "prey" protein or specific binding fragment thereof is specifically localized and restricted to the cytoplasm, or vice versa. The following embodiments are provided as examples. Bait fusions can be made with known endogenous or exogenous transcription inhibitors, for example Gal80p (such a system is termed the "B-80 version"), or bait fusion can be made with multicellular organism-based or synthetic membrane targeting sequences, for example, a myristoylation signal or a mitochondria outer membrane (MOM) targeting signal (B-Myr or B-MOM versions), or any other sequence that specifically localizes or restricts the prey to the cytoplasm. The latter two embodiments have the advantage that libraries (e.g., cDNA libraries), wherein the prey proteins or protein-binding fragments thereof are fused to the transcription inhibitor (to either the N-terminus or C-terminus), can be used with either the B-Myr or B-MOM versions of the desired bait.

As an example of the B-80 version of the methods and reagents of the invention, the protein of interest is fused with the Gal4p inhibitor, Gal80p. Gal80p functions as an inhibitor of Gal4p transcriptional activator and this property is generally retained when other protein sequences are fused to either N- or C-terminus of Gal80p. This retention of native activity advantageously increases the likelihood that bait proteins fused to Gal80p not interfere with Gal80p's ability to inactivate Gal4p transcription activation activity. The invention also provides libraries of either N-terminal or C-terminal fusions, wherein the fusion protein comprises a plurality of fusion proteins in which the transcription inhibitor protein. (such as Gal80p) is fused to each of a plurality of members of said cDNA library in each species of fusion protein comprising said plurality. In these embodiments, the likelihood that bait proteins fused to Gal80p (in this example; to other transcriptional inhibitors in other analogous systems) will fold in a manner that preserves native interacting surfaces is optimized.

For a protein or protein-binding fragment to be tested or in alternative embodiments, wherein the Gal80p fusion is a particular protein of interest and the cytoplasmically-restricted fusion protein comprises a plurality of fusion proteins in which the cytoplasmic localization sequence is fused to each of a plurality of members of said cDNA library in each species of fusion protein comprising said plurality, for cDNA libraries to be screened, cDNAs are preferably cloned into vectors encoding a multicellular organism-based or synthetic myristoylation signal or mitochondria outer membrane-targeting signal. The ability to target proteins to different cellular environments (e.g., the plasma membrane or mitochondrial outer membrane) provides utility for assays involving a protein that may require the particular environment of the cytoplasm or the mitochondrion or the environment proximal to a cellular membrane in the cytoplasm to be fully active and participate in its native interactions. As provided by the invention, such constructs can also advantageously comprise a green fluorescent protein (GFP) tag, or other known tag, for convenient verification of protein expression and targeting.

In particular embodiments, the invention provides methods for detecting protein-protein interactions that occur in a host cell cytoplasm comprising the steps of introducing into a cell from a multicellular organism a gene expressing a first protein or protein-binding fragment thereof fused with the amino- or carboxyl-terminus of Gal80p; introducing into said host cell a gene expressing a second protein or protein-binding fragment thereof fused to a multicellular organism-based or synthetic cytoplasm localization sequence, wherein upon interaction of the first and second proteins in the cell cytoplasm, said Gal80p fusion protein is localized to the cytoplasm, wherein transcription of a gene operably linked to a promoter that is sensitive to or regulated by said transcriptional inhibitor is increased; and detecting said increased transcription of said gene wherein said protein-protein interaction is detected thereby.

In related embodiments, the cytoplasm localization sequence is a membrane targeting sequence, preferably a cell membrane targeting sequence or a mitochondrial membrane targeting sequence. Preferably, the cell is a cell from a multicellular organism. In certain embodiments, the gene operably linked to a promoter that is sensitive to or regulated by Gal80p is an exogenous reporter gene, most preferably encoding a detectable product or a product that produces a detectable metabolite.

In certain related Gal80p-based embodiments, the increased gene expression of the gene operably linked to a promoter that is sensitive to or regulated by Gal80p is a selectable gene, wherein said increased transcription permits growth of the cell in selective conditions. In these embodiments, the inventive methods further comprise subjecting the host cell to selective growth conditions, and detecting increased growth or survival of said cells under selective growth conditions, wherein said protein-protein interaction is detected thereby.

In alternative embodiments, the inventive methods provide a method for isolating a protein that is a member of an interacting protein pair, or a nucleic acid encoding said protein, the method further comprising the steps of isolating the encoding sequence, for example, cDNA sequence, for said second protein and optionally expressing said protein in a host cell.

In preferred embodiments, the first or second protein or protein-binding fragment can be any protein that specifically interacts or, when probing a library for interacting proteins or protein-binding fragments, putatively interacts with another protein in a cell. In certain preferred embodiments, the first protein includes but is not limited to transcriptional proteins or fusions to transcriptional proteins. As used herein the term "transcriptional protein" includes but is not limited to any protein that is involved with or a component of the transcriptional machinery of the cell, including transcriptional activators, transcriptional repressors, RNA polymerase II associated proteins, and chromatin associated proteins. In an additional embodiment, the first protein is encoded by a member of a cDNA library, wherein said library comprises a plurality of fusion proteins in which the transcription inhibitor protein (such as Gal80p) is fused to each of a plurality of members of said cDNA library in each species of fusion protein comprising said plurality.

In further embodiments, the protein or protein-binding fragment "binding partner" (so labeled here to avoid confusion with the "first" or "second" proteins and protein-binding fragments that include or are fused to a transcriptional protein) to the first or second protein or protein-binding fragment described in the above paragraph is a fusion with a cytoplasmic localization sequence, preferably encoded by a cloned cDNA. This binding partner can also be encoded by a member of a cDNA library, wherein the fusion protein comprises a plurality of fusion proteins in which the cytoplasmic localization sequence is fused to each of a plurality of members of said cDNA library in each species of fusion protein comprising said plurality. In additional preferred embodiments, this binding partner is fused to the C- or N-terminus of a membrane targeting sequence, for example, a multicellular organism-based or synthetic membrane targeting sequence. The term "membrane targeting sequence" is intended to encompass DNA sequences that result in membrane localization/anchorage of translated proteins. Membranes in this aspect of the invention include but are not limited to the cell membrane, mitochondrial outer membrane, nuclear membrane, vacuolar membranes, vesicular membranes, membranes of the endoplasmic reticulum, membranes of the Golgi apparatus, and all other organelle membranes. In a preferred embodiment, the binding partner is localized to the cellular membrane via fusion to a myristoylation sequence. In an additional preferred embodiment, the binding partner is localized to the outer mitochondrial membrane via fusion to a Tom70/Mas70 sequence or multicellular species-specific homolog thereof, or any other mitochondrial inner membrane protein or outer membrane protein that protrudes into the cytoplasm.

The invention also provides host cells harboring expression constructs described herein. "Expression constructs" and "recombinant expression constructs" will be understood to be genetically-engineered nucleic acid sequences encoding at a minimum an origin of replication, a selectable marker and a gene comprising a polypeptide-encoding nucleic acid that is expressed in a recipient host cell. In preferred embodiments, recombinant expression constructs can comprise coding sequences for the bait and prey protein-transcription factor fusions as described herein and a coding sequence that encodes a detectable product or causes a detectable phenotype. In other embodiments, cDNAs and galactose regulon components described above can be used in the construction of recombinant expression constructs. In additional embodiments, cDNAs and glucose regulon components described above can be used in the construction of recombinant expression constructs. In certain aspects, the recombinant expression constructs of the invention most preferably comprise coding sequences that encode a transcription inhibitor. The recombinant expression constructs of the invention can encode transcription factors derived from the galactose regulon, preferably Gal80p, and the glucose regulon, for example, Mig1p and Mig2p. The recombinant expression constructs also comprise protein-encoding cDNAs fused to the amino- or carboxyl-terminal sequence of a transcription inhibitor of choice, for example, Gal80p (galactose regulon) or Mig1p (glucose regulon). In a further embodiment, the recombinant expression constructs comprise protein-encoding cDNAs fused to membrane targeting peptides. In additional embodiments, the recombinant expression constructs encode membrane targeting signal peptides fused to protein-independent encoding cDNAs or a plurality of protein-encoding cDNAs in one or more cDNA libraries. In a preferred embodiment, the expression constructs further encode a myristoylation sequence or a membrane targeting sequence, for example, Tom70/Mas70 for yeast, or known membrane targeting sequence applicable to the multicellular species of interest, or of synthetic origin.

In a further embodiment, the selectable growth conditions are chosen to select for multicellular organisms or cells therefrom comprising a selectable reporter gene wherein increased expression thereof confers a growth advantage on the cell or distinguishes the cell in a detectable manner. In these embodiments, protein-protein interactions are determined by expression of selectable or detectable reporter genes, or subsequent growth of the host cell arising from expression of a selectable reporter gene, or a combination thereof. In this embodiment, protein-protein interaction permits transcriptional activation and expression of a selectable or detectable reporter gene, or subsequent growth of the host cell arising from expression of a selectable reporter gene, or a combination thereof. In the practice of one aspect of this embodiment of the invention, the selectable reporter gene is expressed to high enough expression levels to provide sufficient production of the gene product to permit cell growth under selectable conditions.

In additional related embodiments, the selectable reporter gene encodes a product that converts a non-toxic compound to a cytotoxic or cytostatic compound. In such embodiments, decreased expression of said gene is detected by cell growth or survival; whereas, increased expression of said gene is detected by cell death.

In a further embodiment, the invention provides methods for detecting protein-protein interactions by expression of a detectable or selectable reporter gene. A detectable reporter gene as used in these methods is any that is detectable, for example visibly, by the presence of the gene product. Examples of selectable reporter genes include but are not limited to green fluorescence protein (GFP), cyan fluorescence protein (CFP), yellow fluorescent protein (YFP), the red fluorescent protein DsRed, beta-glucoronidase, luciferase, and lacZ (encoding beta-galactosidase). A selectable reporter gene as used in these methods is any that can be used to, for example, enable or prevent the growth of a cell expressing said gene. Examples of selectable reporter genes include but are not limited to HIS3, ADE2, ADE5, ADE7, LYS2, LEU2, URA3, TRP1, KAN, NEO (neomycin resistance for growth in G-418), growth on hypoxanthine-aminopterin-thymidine (HAT) media for thymidine kinase, growth in the presence of pyrimidine analogs such as bromodeoxyuridine (BrdU) for thymidine kinase activity, and growth in methotrexate for dihydrofolate reductase (DHFR). The detectable reporter gene or genes utilized may not be the same gene or genes utilized as the selectable reporter gene (i.e., a gene required for growth). In another embodiment of this aspect of the inventive methods, protein-protein interaction is detected by reporter gene activity. Reporter gene activity may be determined by growth (i.e., using a selection protocol), or biochemical activity, or a biophysical signal such as fluorescence, photon emission, change in color spectrum, transfer of radioactive groups, or by binding to an antibody and detected either directly or indirectly, for example, by conjugation to a detectable marker such as horseradish peroxidase or a fluorescent agent.

The expression of all selectable or detectable reporter genes is dependent on the activation of upstream promoters. Upstream promoters have required DNA sequence(s) for binding transcriptional activator(s) or a site-specific DNA-binding domain that is fused to a transcription activation domain, for example, the Gal4p transcriptional activation domain and, optionally, for binding a transcriptional inhibitor directly. Transcription of selectable or detectable reporter genes is dependent on binding a transcription activator protein, for example Gal4p or its transcription activation domain to the promoter and the absence of binding of a transcription inhibitor, for example Gal80p, either to a binding domain on the transcriptional activator protein or on the DNA itself. Thus, when the promoter has transcriptional activating activity and a less than inhibitory amount of inhibition activity (e.g., when a transcriptional inhibitor is sequestered in the cytoplasm by a protein anchored to a membrane), the selectable or detectable gene can be transcribed. Growth under the appropriate selection conditions for the selectable marker or detection of a detectable marker demonstrates protein-protein interactions occurred between the prey and bait proteins. For example, where the native Gal4p is used, the expression of all selectable or detectable reporter genes is dependent on the activation of upstream GAL gene promoters having a $UAS_{GAL}$ DNA sequence by binding Gal4p to the promoter and sequestration of the Gal80p transcription inhibitor in the cytoplasm.

The term "GAL gene promoter" is intended to encompass any regulatable promoter isolated from any of the genes of the yeast galactose regulon including but not limited to GAL1, GAL7, GAL10, GAL2, GAL5, MEL1 and other native GAL gene promoters indigenous to yeast as well as all artificial, man-made galactose-responsive promoters that are under the control of the GAL gene promoter specific $UAS_{GAL}$ sequences and the $UAS_{GAL}$-specific transcriptional activator, Gal4p or derivatives of Gal4p that retain the DNA binding domain and the Gal80p-binding domain of Gal4p. Alternatively, Gal4-activatable promoters having synthetic $UAS_{GAL}$ sites can be utilized to drive induced expression of polypeptides.

The term "detectable" refers herein to the ability to identify, measure, or localize a protein product, either antigenically, immunologically or enzymatically within the host cell or cell extracts. Protein products can further comprise additional sequences useful for promoting identification or purification of the protein, such as epitope or fluorescent tags. Examples of such epitope and fluorescent tags include, but are not limited to FLAG (Sigma Chemical, St. Louis, Mo.), myc (9E10) (Invitrogen, Carlsbad, Calif.), 6-His (Invitrogen; Novagen, Madison, Wis.), HA (Boehringer Manheim Biochemicals), green fluorescent protein (GFP), cyan fluorescent protein (CFP), and the red fluorescent protein DsRed. In one embodiment, polypeptide sequences, or fragments thereof, are operatively linked to a nucleic acid sequence encoding an "epitope tag", so that the protein is expressed with an epitope tag. The epitope tag may be expressed as the amino terminus, the carboxyl terminus, or internal to any of the polypeptide chains comprising any of said first protein second protein, or Gal80p so long as the resulting protein remains functional and is able to interact with other proteins.

The term "isolating" refers to any methods known in the art for isolating or purifying DNA. In the practice of certain aspects of this invention, plasmids containing cDNAs of interest are isolated from multicellular organisms or cells therefrom and transformed into *E. coli* for subsequent amplification, purification, and characterization. (Ward, 1990 *Nucleic Acids Research* 18: 5319). Such methods for isolation include but are not limited to PCR amplification, SDS-alkaline lysis, lithium chloride/Triton® X-100, resin-based isolation, and introduction into *E. coil*, restriction digestion, any other methods known in the art or any combination thereof.

The term "selectable gene" generally refers to a coding sequence that encodes a product, the presence or absence of which can be detected. For example, increased expression of said selectable gene can confer a growth advantage or a growth disadvantage on the cell or can distinguish the cell in some detectable manner. Likewise, decreased expression of said selectable gene can confer a growth advantage or a growth disadvantage on the cell or can distinguish the cell in some detectable manner. Thus, as used herein, said selectable genes can be useful in positive as well as negative selection method, as known in the art.

The invention also provides methods for detecting in a host cell cytoplasm a nuclear export sequence (NES), the method comprising the steps of introducing into the cell a recombinant expression construct encoding a protein or protein-binding fragment containing a putative NES fused with the amino- or carboxyl-terminus of a transcription inhibitor; assaying the cell for expression of a gene operably linked to a promoter that is sensitive to or regulated by said transcriptional inhibitor; and detecting increased expression of said gene, wherein an NES is detected thereby.

In certain aspects of the invention, the transcription inhibitor is any endogenous transcription factor from the multicellular organism or cell therefrom, preferably transcription inhibitor, or exogenous transcription factor, also preferably a transcription inhibitor. In particular embodiments, the transcriptional inhibitor is Gal80p. In a preferred embodiment, the recombinant expression construct encodes a cDNA or a member of a cDNA library, wherein said library comprises a plurality of fusion proteins in which the transcription inhibitor protein (such as Gal80p) is fused to each of a plurality of members of said cDNA library in each species of fusion protein comprising said plurality. Also preferred are methods wherein the gene, or coding sequence thereof, that is operably linked to a promoter that is sensitive to or regulated by said transcriptional inhibitor is a selectable gene, wherein increased expression of said gene confers a growth advantage on the cell. In these embodiments, the inventive methods further comprise subjecting the host cell to selective growth conditions, and detecting increased growth or survival of said cells under selective growth conditions, wherein said protein-protein interaction is detected thereby. In another embodiment, the gene or coding sequence thereof that is operably linked to a promoter that is sensitive to or regulated by a transcriptional inhibitor encodes a detectable protein product.

The invention also provides methods for isolating NES, the method comprising detecting increased expression of a gene operably linked to a promoter that is sensitive to or regulated by said transcriptional inhibitor in a cell comprising a recombinant expression construct encoding a protein or protein-binding fragment containing a putative NES fused with the amino- or carboxyl-terminus of a transcription inhibitor; and isolating said recombinant expression construct comprising said NES from the cell.

Also preferred are embodiments wherein gene operably linked to a promoter that is sensitive to or regulated by a transcriptional inhibitor is an exogenous reporter gene encoding a detectable product. In further preferred embodiments, the gene operably linked to a promoter that is sensitive to or regulated by a transcriptional inhibitor is a selectable gene, wherein increased expression of said gene confers a growth advantage on the cell. In these embodiments, the method further comprises the steps of subjecting the host cell to selective growth conditions, and detecting increased growth or survival of said cells under selective growth conditions, wherein said NES is detected thereby.

The NES can be isolated from a recombinant expression construct comprising a cell expressing a gene operably linked to a promoter that is sensitive to or regulated by said transcriptional inhibitor.

In an additional preferred embodiment, the invention includes methods for detecting proteins or protein-binding fragments thereof containing nuclear export sequence (NES). A cDNAs or plurality thereof that encodes a protein or proteins containing an NES sequence are fused to a transcriptional inhibitor, for example, Gal80p. The presence of an exogenous nuclear export sequence in said protein results in sequestration of the transcription inhibitor in the cytoplasm and subsequent activation of one or more promoters that correspond or are sensitive to the transcription inhibitor.

The invention also provides a method for detecting a nuclear localization sequence (NLS) in a host cell comprising introducing into the cell a recombinant expression construct encoding a protein or protein-binding fragment containing a putative NLS fused with the amino- or carboxyl-terminus of a transcription inhibitor; assaying the cell for expression of a gene operably linked to a promoter that is sensitive to or regulated by said transcriptional inhibitor; and detecting decreased expression of said gene, wherein an NLS is detected thereby.

In a preferred embodiment, the recombinant expression construct encodes a cDNA or a member of a cDNA library, wherein the recombinant expression construct encodes a fusion protein and wherein the library thereof encodes a plurality of fusion proteins in which the transcription inhibitor protein (such as Gal80p) is fused to each of a plurality of members of said cDNA library in each species of fusion protein comprising said plurality, wherein certain of the members of the cDNA species comprise an NLS. Also preferred are methods wherein the gene that is operably linked to a promoter to or regulated by said transcriptional inhibitor encodes a product that converts a non-toxic compound to a cytotoxic or cytostatic compound. In additional preferred embodiments, expression of the gene that is operably linked to a promoter to or regulated by said transcriptional inhibitor is inducible when the cell is contacted with an inducing agent. In preferred embodiments, the gene that is operably linked to a promoter sensitive to or regulated by said transcriptional inhibitor encodes a product that converts a non-toxic compound to a cytotoxic or cytostatic compound and wherein the expression of the gene operably linked to a promoter that is sensitive to or regulated by said transcriptional inhibitor is inducible when the cell is contacted with an inducing agent. In such embodiments, decreased expression of said gene is detected by cell growth or survival when the cell is contacted with both the inducing agent and the cytotoxic or cytostatic compound.

The invention also provides methods for isolating NLS, the method comprising the steps of detecting decreased expression of the gene operably linked to a promoter that is sensitive to or regulated by said transcriptional inhibitor and encoded by a recombinant expression construct encoding a NLS-containing protein or NLS-containing fragment thereof fused with the amino- or carboxyl-terminus of a transcription inhibitor; and isolating said recombinant expression construct comprising said NLS from the cell. The invention also provides methods for isolating NLS, the method comprising the steps of transfecting In a further embodiment, the invention provides a method for detecting proteins or fragments thereof containing one or more nuclear localization sequence. In the practice of this aspect of the invention, cDNAs encoding proteins containing a putative NLS are fused to a transcription inhibitor such as, for example, Gal80p. The presence of an exogenous nuclear localization sequence in said protein results in sequestration of the transcriptional inhibitor in the nucleus and limits its export to the cytoplasm. In the nucleus, the transcription inhibitor inhibits gene expression. Preferably, gene expression imposes a growth disadvantage on said cells, so that cells comprising said transcription inhibitor-NLS fusion have a growth advantage. In certain related embodiments, any NLSs that are native to the transcriptional inhibitor can be deleted or mutated (i.e., rendered non-functional or of limited function) prior to fusion to putative NLS-containing proteins or protein-binding fragments. In such embodiments, basal-level expression of the gene operably linked to the promoter that is sensitive to or regulated by said transcriptional inhibitor can be greatly increased, thereby enhancing the signal of any non-native NLS introduced in the methods herein. Such an embodiment is particularly useful when the product of the gene operably linked to the promoter that is sensitive to or regulated by said transcriptional inhibitor encodes a product that can convert a non-toxic compound to a cytotoxic or cytostatic compound, or simply encodes a toxic or cytostatic product itself. The presence of a NLS decreases the expression of a product that is cytotoxic or cytostatic, thus conferring a growth advantage on those cells that have had a functional NLS fused to the protein or protein-binding fragment. Gal80p, for example, is known to have a bipartite NLS signal, or two nonadjacent NLSs. (Nogi, Y. and Fukasawa, T., Molecular and Cellular Biology 1989 9:3009–3017). Deletion of one or both of the NLSs increases the mean residence time of Gal80p in the cytoplasm, thus increasing the basal transcription of a gene operably linked to the promoter that is sensitive to or regulated Gal80p. Thus, when a coding sequence, for example, from a cDNA library, that is fused to a Gal80p that has had its native NLSs mutated or deleted actually encodes an exogenous NLS, the Gal80p-based fusion will be targeted to the nucleus. A Gal80p-based fusion protein residing in the nucleus will interact with Gal4 and inhibit expression of a gene operably linked to the promoter that is sensitive to or regulated by Gal80p. When said gene encodes a product that can convert a non-toxic compound to a cytotoxic or cytostatic compound, or simply encodes a toxic or cytostatic product itself, suppression of its expression confers a growth advantage over cells with no functional, exogenous NLS sequence fused to the NLS-deleted Gal80p. Such a method provides a powerful selection mechanism for isolating NLSs.

The methods and reagents of the invention can be for galactose-independent inducible gene expression. In the practice of these methods of the invention, one or more recombinant expression constructs can be introduced into the cell from a multicellular organism encoding i) a fusion between a first interacting protein or protein-binding fragment and the amino- or carboxy-terminal of a transcriptional inhibitor (for example Gal80p); ii) a fusion between a second interacting protein or protein-binding fragment and a cytoplasm localization sequence as described above; and iii) a coding sequence operably linked to a promoter that is sensitive to or regulated by said transcriptional inhibitor. As galactose mediates the interaction between Gal80p and Gal3p, other molecules (either protein or non-protein based) can induce interaction between two proteins or protein-binding fragments, one of which can be fused to the amino- or carboxy-terminal of a transcriptional inhibitor and the other of which can be fused to a cytoplasm localization sequence as described hereinabove. Thus, any complex of three interacting proteins known in the art can be utilized, recombinantly, in a multicellular organisms or cells therefrom, to comprise reagents for the methods of this embodiment of the invention, one a fusion to the transcription inhibitor, the second as a fusion to a cytoplasm localization sequence, and the third (the protein in the protein complex binds the two others, i.e., the protein in the middle of the complex) can act as the inducer or transcription.

Thus, introduction of such a non-galactose inducing agent can facilitate the interaction between the first and second fusion proteins, thus preferentially sequestering or trapping the transcription inhibitor in the cytoplasm. The preferential sequestration or trapping of the transcription inhibitor in the cytoplasm reduces its ability to suppress expression of a coding sequence operably linked to a promoter that is sensitive to or regulated by said transcriptional inhibitor. Consequently, transcription of the coding sequence operably linked to a promoter that is sensitive to or regulated by said transcriptional inhibitor is stimulated. Preferentially, the coding sequence encodes a detectable or selectable product thus enabling easy determination of altered expression levels of the operably-linked coding sequence. In alternative embodiments, putative or potential inducing agents can be screened for activity by exposing the multicellular organisms or cells therefrom of this aspect of the invention to the putative inducing agent. Increased expression of the coding sequence operably-linked to a promoter that is sensitive to or regulated by a transcriptional inhibitor fused to the first interacting protein or protein-binding fragment, indicates positive inducing activity, or the ability to an facilitate interaction between the first interacting protein or protein-binding fragment-fusion and the second interacting protein or protein-binding fragment-fusion. Decreased expression of said coding sequence can indicate negative inducing activity, or anti-inducing activity. For example, the agent inhibits interactions between said first and second interacting proteins or protein-binding fragments. Unaltered expression of said coding sequence can indicate a lack of inducing activity. Thus, the invention provides methods for galactose-independent inducible gene expression and methods of screening potential inducing agents.

The invention also provides methods for regulatable gene expression in multicellular organisms or cells therefrom comprising the steps of introducing a recombinant expression construct encoding Gal80p into the cell from a multicellular organism, introducing a recombinant expression construct encoding Gal3p into the cell from a multicellular organism, introducing a recombinant expression construct encoding Gal4p into the cell from a multicellular organism, introducing a coding sequence operably linked to a promoter sensitive to or regulated by Gal3p/Gal4p/Gal80p, and treating the cell from a multicellular organism with an inducing agent, wherein treatment mediates the cytoplasmic interaction of the Gal3p and Gal80p, relieving Gal80p inhibition and permitting Gal4p activation of the coding sequence operably linked to the promoter sensitive to or regulated by the Gal80p, Gal3p and Gal4p, wherein the promoters are fused to a heterologous gene. In certain embodiments, the inducing agent is galactose. In other embodiments, Gal4p or a fragment thereof is expressed from a heterologous Gal4p gene introduced into the multicellular organisms or cells therefrom. In still other embodiments, the coding sequence is operably linked to a promoter sensitive to or regulated by Gal3p, Gal4p and Gal80p are expressed from $UAS_{GAL}$-containing promoters. In the practice of certain aspects of this invention, a gene or coding sequence of interest, which can be any coding sequence (including heterologous sequences), is operably coupled to a promoter sensitive to or regulated by Gal4p and introduced into the cell from a multicellular organism, for example, on an expression vector or by integrating into the host genome. In such embodiments, a gene or coding sequence encoding Gal80p protein and Gal3p are introduced into the cell from a multicellular organism, for example, on an expression vector or by integrating into the host genome. As discussed above, Gal80p, which is an inhibitor of the transcriptional activator Gal4p, binds with high affinity to a specific portion of the Gal4p transcriptional activation domain, and blocks Gal4p's ability to recruit RNA polymerase II at $UAS_{GAL}$ sites contained in GAL gene promoters. However, Gal80p's binding within the Gal4p transcriptional activation domain (and resulting suppression of transcription of the gene or coding sequence of interest) is relieved by the interaction between Gal3p and Gal80p, an interaction that occurs only in the presence of galactose. In the presence of galactose, Gal80p, binds to Gal3p molecules that are normally confined to the cytoplasm in the cell from a multicellular organism, resulting in insufficient Gal80p in the nucleus to inhibit Gal4p and consequent expression of the gene or coding sequence of interest. Consequently, Gal4p is able to activate genes of the galactose regulon, as well as reporter genes expressed via $UAS_{GAL}$ promoters. Preferably, the gene or coding sequence of interest encodes a product that is detectable, thus enabling the detection of the regulatable gene expression in multicellular organisms or cells therefrom.

In a related embodiment, the invention provides methods for regulatable gene expression in multicellular organisms or cells therefrom comprising the steps of introducing a recombinant expression construct encoding Gal80p into the cell from a multicellular organism, introducing a recombinant expression construct encoding Gal3p into said cell from a multicellular organism, introducing a recombinant expression construct encoding Gal4p or a fragment thereof fused to a transcription factor or DNA-binding portion thereof into said cell of a multicellular organism, wherein the transcription factor or DNA binding fragment thereof is a transcription factor from a multicellular organism, introducing a coding sequence operably linked to a promoter sensitive to or regulated by the transcription factor, and treating the cell from a multicellular organism with an inducing agent, wherein treatment mediates the cytoplasmic interaction of the Gal3p and Gal80p, relieving Gal80p inhibition of the Gal4p-transcription inhibitor fusion protein and permitting activation of the coding sequence operably linked to the promoter sensitive to or regulated by the transcription factor. In certain embodiments, the coding sequence operably linked to the promoter sensitive to or regulated by the transcription factor is an endogenous gene. In other embodiments, the promoter sensitive to or regulated by the transcription factor is an endogenous promoters. In still other embodiments, the promoters operably linked to a heterologous gene. In yet further embodiments, the coding sequence operably linked to the promoter sensitive to or regulated by the transcription factor is a reporter gene. Preferably, the gene or coding sequence of interest encodes a product that is detectable, thus enabling the detection of the regulatable gene expression in multicellular organisms or cells therefrom. In other embodiments, the inducing agent is galactose. In the practice of certain aspects of this invention, a gene or coding sequence of interest, which can be any coding sequence (including heterologous sequences), is operably coupled to a promoter sensitive to or regulated by the transcription factor and introduced into a cell from a multicellular organism, for example, on an expression vector or by integrating into the host genome. In such embodiments, a gene or coding sequence encoding Gal80p protein and Gal3p are introduced into the cell from a multicellular organism, for example, on an expression vector or by integrating into the host genome. As discussed above, Gal80p, which is an inhibitor of the transcriptional activator Gal4p, binds with high affinity to a specific portion of the Gal4p transcriptional activation domain, and blocks Gal4p's ability to recruit RNA polymerase II and other transcriptional machinery to the promoter. In this aspect of the invention, Gal4p, or a fragment thereof, does not interact directly with the promoter; rather, the transcription factor, or DNA-binding domain thereof, to which the Gal4p or fragment thereof is fused binds to the promoter that is sensitive to or regulated by said transcription factor. Nevertheless, the Gal4p or fragment thereof (preferably a fragment that interacts with Gal80p) can, for example, recruit RNA polymerase II to the promoter that in the absence of Gal80p repression. Thus, in the presence of an inducing agent such as galactose, Gal80p binds to Gal3p molecules that are normally confined to the cytoplasm, resulting in insufficient Gal80p in the nucleus to inhibit the Gal4p-based repression of the transcription factor to which it is fused causing, in this example, expression of the gene or coding sequence of interest. Similarly, the transcription factor to which Gal4p or a fragment thereof is fused can be a transcription activator. Transcription factors useful in the practice of this aspect of the invention include but are not limited to $NF_6B$, AP-1, AP-2, Sp-1, CRE, CREB, Myo-D1, TBP, TFIIH, ER, STAT-1, and STAT-2.

The following examples illustrate certain aspects of the above-described invention and advantageous results thereof. The following examples are shown by way of illustration and not by way of limitation. The disclosure of each reference cited herein is explicitly incorporated by reference. Examples in yeast are provided as background for the present invention relating to multicellular organisms or cells therefrom.

EXAMPLE 1

Preparation of Plasmids Containing Membrane Targeting Sequences and Localization of Fusion Protein Expression in Yeast To determine if Gal80p would interact with a membrane-bound binding partner, Gal3p (Gal80p's natural binding partner) was tethered to the cell and mitochondrial membranes. In addition, the effects of Gal3p sequestration on galactose induction of GAL gene expression were examined.

Gal3p-GFP was targeted to the cytoplasmic or mitochondrial outer membranes by fusion to a protein myristoylation signal (Myr-Gal3p-GFP) or mitochondrial outer membrane signal anchor sequence (MOM-Gal3p-GFP), respectively. N-myristoylation (Johnson et al., 1994, *Annu. Rev. Biochem.* 63: 869–914; Resh et al., 1999, *Biochem. Biophys. Acta.* 1451: 1–16) was chosen because it is a co-translational process that occurs when the nascent peptide is still attached to the ribosome. Mitochondria targeting was chosen because it appears to be a very fast and efficient process (Fujiki and Verner, 1993, *J. Biol. Chem.* 268: 1914–20; Funfschilling et al., 1999, *Mol. Biol. Cell.* 10: 3289–99).

Ga13p derivatives (including Gal3p-GFP derivatives) bearing protein N-myristoylation signals were generated by inserting oligonucleotides encoding each signal peptide sequence into GAL3 gene at the N terminus. The N-myristoylation signals used herein are: MGCTVSTQTIGDESDP (SEQ ID NO:1), obtained from the N-terminal domain of Gpa1p (a G protein α subunit), a N-myristoylation signal variant MACTVSTQTIGDESDP (SEQ ID NO:2) (the single G→A substitution abolishes the acylation and membrane targeting), or the mitochondria outer membrane signal anchor sequence (the first 29 amino acid residues of Tom70p (MKSFITRNKTAILATVAATGTAIGAYYYY (SEQ ID NO:3)), a component of the translocase of the outer mitochondrial membrane complex). It has been shown that the N-myristoylation signal used here is sufficient to target a heterologous protein to the plasma membrane (Gilen et al., 1992, *J. Cell. Sci.* 111: 323544). The first 29 amino acids of Tom70p protein is sufficient to target a heterologous protein to the outer membrane of mitochondria, leaving the bulk of protein extruding into the cytoplasm (McBride et al., 1992, *J. Cell. Biol* 119: 1451–1457). The ADH2 promoter, FPR1, CNA1, HOM3 and CMD1 sequences were PCR amplified using yeast Sc723 genomic DNA as the template and oligonucleotide primers disclosed in the Examples below. Green fluorescence protein (GFP) and cyan fluorescence protein (CFP) sequences were PCR amplified using pYGFP1 (Cormack et al., 1996, *Gene* 173: 33–38) and pDH3 (Yeast Resource Center, University of Washington) as template, respectively.

Plasmid constructions to generate the Myr-Gal3, mMyr-Gal3 and MOM-Gal3 plasmids were prepared as follows. Myr-Gal3 and mMyr-Gal3 fusions were constructed in plasmid pTEB16, a low-copy number yeast shuttling plasmid having a TRP1 marker (Blank et al. 1997, *Mol Cell Biol.* 17: 2566–75). A SpeI site and a PstI site were created at the N terminus of GAL3 in pTEB16 (Peng and Hopper, 2000, *Molec. Cell Biol.* 20: 5140–8). The oligonucleotides GANG49/50 encoding MGCTVSTQTIGDESDP (SEQ ID NO:6) were annealed and inserted at SpeI/PstI site to generate Myr-Gal3 construct. An identical procedure was used to create a mMyr-Gal3 bearing plasmid. The MOM-Gal3 plasmid (containing MOM targeting sequence, HA tag, GFP and GAL3) was constructed in plasmid pTEB16, a low-copy number yeast shuttling plasmid having a TRP1 marker (Blank et al., 1997, *Mol. Cell. Biol.* 17: 2566–75). A SpeI site and a PstI site were created at the N terminus of GAL3 in pTEB16 (Peng and Hopper, 2000, *Mol. Cell. Biol.* 20: 5140–8). The oligonucleotides GANG53/55 and GANG54/56 were annealed separately and then inserted at SpeI/PstI site to add the MOM targeting sequence. The oligonucleotides GANG59/60 were annealed and inserted at the PstI site to add the hemagluttinin (HA) tag. The PCR product using pYGFP1 (Cormack et al., 1996, *Gene* 173: 33–8) as template and GANG31/61 as primers was cut with PstI and inserted at PstI site to add the GFP sequence.

The oligonucleotides and the references relating to the constructions of the Myr-Gal3-GFP, mMyr-Gal3-GFP and MOM-Gal3-GFP plasmids are provided below.

MOM-Gal3p-GFP were examined by fluorescence microscopy using a Nikon Optiphot-2 epifluorescence microscope equipped with a 100× objective. GFP was excited and its emission fluorescence was detected using Chroma filter #41017 (Chroma Technology Corp., Brattleboro, Vt.). Images were acquired using a SenSys KF1400 CCD camera (Photometrics Ltd, Tucson, Ariz.), controlled by QED (Pittsburgh, Pa.) software.

Thus, fusion of Gal3p to membrane targeting sequences resulted in appropriate localization of Gal3p at the cell and mitochondrial membranes.

EXAMPLE 2

Membrane Associated Gal3p Retains Ability to Bind Gal80p and Induce GAL Gene Expression in Yeast To verify appropriate activity of Myr-Gal3p or MOM-Gal3p in yeast cells harboring the plasmids encoding these

TABLE 1

Oligonucleotide Primers

| | | | |
|---|---|---|---|
| GANG31 (SEQ ID NO:7) | PstI-GFP forward | AAC TGC AGG TAT GTC TAA AGG TGA AG | |
| GANG49 (SEQ ID NO:8) | Myr/palm signal-1 | CTA GTA TGG GGT GTA CAG TGA GTA CGC AAA CAA TAG GAG ACG AAA GTG ATC CTT CTG CA | |
| GANG50 (SEQ ID NO:9) | Myr/palm signal-2 | GAA GGA TCA CTT TCG TCT CCT ATT GTT TGC GTA CTC ACT GTA CAC CCC ATA | |
| GANG53 (SEQ ID NO:10) | Tom70 (29)-1-sense | CTA GTA TGA AGA GCT TCA TTA CAA GGA ACA AGA CAG CCA TTT TGG CAA | |
| GANG54 (SEQ ID NO:11) | Tom70(29)-2-sense | CCG TTG CTG CTA CAG GTA CTG CCA TCG GTG CCT ACT ATT ATT ACG GTG CTG CA | |
| GANG55 (SEQ ID NO:12) | Tom70(29)-1-antisense | GCA ACG GTT GCC AAA ATG GCT GTC TTG TTC CTT GTA ATG AAG CTC TTC ATA | |
| GANG56 (SEQ ID NO:13) | Tom70(29)-2-antisense | GCA CCG TAA TAA TAG TAG GCA CCG ATG GCA GTA CCT GTA GCA | |
| GNAG59 (SEQ ID NO:14) | Linker/HA for Tom70-3-sense | CAG TTG GGT GGT GGT GGT CGT TAC CCA TAC GAC GTC CCA GAC TAG GCT GCA | |
| GANG60 (SEQ ID NO:15) | Linker/HA for Tom70-3-antisense | GCG TAG TCT GGG ACG TCG TAT GGG TAA CGA CCA CCA CCA CCC AAC TGT GCA | |
| GANG61 (SEQ ID NO:16) | PstI-GFP w/o stop | AAC TGC AGA TTT GTA CAA TTC ATC CAT AC | |
| GANG113 (SEQ ID NO:35) | CmdI-SphI/CIaI-forward | AAA AAA GTA CAg cat gca aAT GTC CTC CAA TGT TAG CGA AG | |
| GANG114 (SEQ ID NO:36) | CmdI-SphI/CIaI-reverse | GAT GCA CCT Aat cga ttT TTA GAT AAC AAA GCA GCG AAT TG | |

After addition of these respective targeting signals, Myr-Gal3p-GFP expressed using these constructs localized to the plasma membrane and MOM-Gal3p-GFP expressed using these constructs localized to the mitochondria. In contrast, wild type Gal3p-GFP was shown to be located throughout the cytoplasm, as was Gal3p-GFP joined to the variant N-myristoylation signal having a single amino acid substitution that cannot be acylated. These results are shown in FIG. 1A. The expression patterns of Myr-Gal3p-GFP and fusion proteins, semi-quantitative colony growth assays and galactose-responsive reporter gene analyses were performed. Following verification of appropriate Gal3p expression, the distribution of Gal80p in Myr-Gal3p or MOM-Gal3p expressing cells was examined by fluorescence microscopy and Western blot analysis.

Gene expression was determined for two different types of GAL gene promoters in cells carrying the membrane bound and cytoplasm sequestered Gal3p. First, a sensitive and semi-quantitative colony growth assay was used to assess expression of a HIS3 reporter gene whose promoter bears four UAS$_{GAL}$ sites. Cells of a gal3Δgal1Δ strain (Sc781) carrying Myr-Gal3p or MOM-Gal3p grew indistinguishably from cells harboring wild type Gal3p on synthetic medium lacking histidine in these assays. Because growth rates are proportional to the level of HIS3 gene expression and HIS3 gene expression is proportional to the level of Gal3p activity, we concluded that Myr-Gal3p and MOM-Gal3p are as active as native Gal3p (data not shown). Second, expression of MEL1, a galactose-responsive gene whose promoter bears a single UAS$_{GAL}$ site was quantified. See Lazo et al., 1977, *Eur. J. Biochem.* 77: 375–382; Buckholz and Adams, 1981, *Molec. Gen. Genet.* 182: 77–81; Post-Beittenmiller et al., 1984, *Molec. Cell. Biol.* 4: 1238–1245.

Despite effective sequestration of Gal3p to the cell cytoplasmic membranes, the MEL1 gene was expressed up to wild type levels upon galactose induction (these results are shown in FIG. 1B). The level of MEL1-encoded α-galactosidase in the extracts of cells carrying Myr-Gal3p was not significantly different from that detected in extracts of cells carrying wild type Gal3p (p>0.1, Student's t-test), or carrying a mMyr-Gal3p variant that abolished plasma association (p>0.1). The mitochondria associated Gal3p (MOM-Gal3p) gave rise to higher MEL1 expression than the wild type Gal3p did (p<0.05). Using Western analyses, it was found that membrane association of Gal3p did not increase steady state levels of Gal3p. Cellular levels of Myr-Gal3p and the mMyr-Gal3p variant were slightly lower than that of wild type Gal3p, while the MOM-Gal3p level was similar to that of wild type Gal3p (data not shown). Thus, Myr-Gal3p, mMyr-Gal3p and MOM-Gal3p are all synthesized to similar levels.

Figure 2:
FIGS. 2A through 2C. (Yeast cells) Lowering Gal3p expression levels causes reduction in GAL gene expression.
Figure 2:
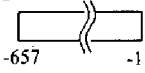
Figure 2:
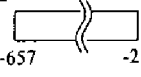
Figure 2:
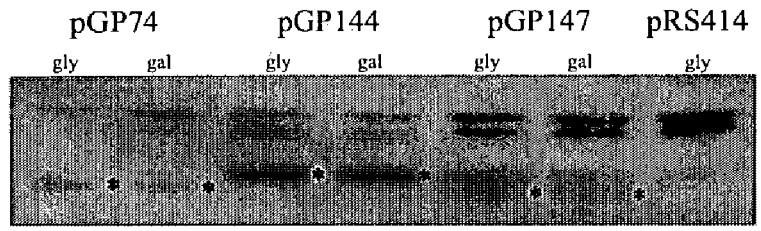

Several lines of evidence indicated that the full induction of GAL genes observed in cells harboring membrane-bound Gal3p was due to the interaction between Gal3p and Gal80p at the cytoplasmic membranes. First, the targeting methods employed were very effective in sequestering Gal3p to the membranes. Based on cell fractionation and Western analyses, essentially all the Gal3p in these cells was associated with the membrane when expressed joined to a myristoylation signal. For the mitochondria-targeted Gal3p, less than about 10% of MOM-Gal3p was found in the soluble cytoplasmic fraction (data not shown). Second, Gal80p redistributed to the plasma membrane and the intracellular vesicle membrane in cells expressing Myr-Gal3p (shown in FIG. 1C). Lastly, a small fraction of Gal3p that might have escaped the cytoplasmic sequestering methods used herein would not have been sufficient to give rise to the levels of GAL gene expression observed in these experiments (shown in FIG. 2). Three plasmids providing different subcellular locations and expression levels of Gal3p were constructed and expression levels of the MEL1 gene in cells carrying these plasmids were determined. The results showed that a five-fold reduction of Gal3p resulted in a two-fold reduction in MEL1 gene expression level, indicating that Gal3p is not in large excess in the cells and that quantitative interactions between Gal3p and Gal80p are required for the transcription of GAL genes. In comparison, a two-fold reduction of Gal3p derivative was observed in cells carrying Myr-Gal3p and resulted in 20% reduction in MEL1 gene expression level.

In summary, these results demonstrated that Gal3p maintains its induction function and its induction capacity and that active transcription of GAL genes in cells harboring Myr-Gal3p is due to the Gal3p-Gal80p interaction at the plasma and vesicular membranes outside the nucleus, rather than to Gal3p interaction with the Gal80p-Gal4p complex in the nucleus. Additionally, the interaction between Gal80p and membrane bound Gal3p resulted in the appropriate activation of GAL reporter gene expression within the nucleus.

EXAMPLE 3

Gal80p Association with Gal4p within Gene Promoters is Reduced in Yeast

Because the association of Gal80p with Gal4p at a GAL gene promoter is essential for inhibition of Gal4p in the absence of galactose, the effect of galactose (which triggers the interaction between Gal3p and Gal80p) on the amount of Gal80p complexed with DNA-bound Gal4p was determined (Torchia et al., 1984, *Mol. Cell Biol.* 4: 1521–1527; Lohr et al., 1987, *J. Biol. Chem.* 262: 15589–15597). To determine the extent of Gal4p and Gal80p association with the UAS-GAL region of the GAL1/GAL10 gene promoter, formaldehyde-based in vivo cross-linking assays were performed followed by chromatin immunoprecipitation.

Chromatin immunoprecipitations were performed as described by Braunstein et al., 1993, *Genes Dev.* 7: 592–604 and Kuras et al. 1999, *Nature* 399: 609–613. Briefly, wild type Sc723 cells (Blank et al., 1997, *Mol. Cell. Biol.* 17: 2566–2575) were grown to early exponential growth phase (as measured by absorbance at 600 nm~0.4) in 250 mL yeast extract-peptone medium containing 2% glycerol, 3% lactic acid, and 0.05% glucose (-galactose, un-induced). For galactose-induced cultures, galactose was added to the un-induced cultures to a final concentration of 2% and the cultures were incubated for an additional 20 minutes. Formaldehyde was added to a final concentration of 1%, the cultures were incubated for 20 minutes at room temperature, and glycine was added to a final concentration of 300 mM. All the following steps were carried out at 4° C. Cells were washed twice with TBS (20 mM Tris-HCl, 150 mM NaCl, pH 8.0), resuspended in 1 mL lysis buffer (50 mM Tris-HCl pH 8.0, 10 mM EDTA, 1% SDS, 1 mM PMSF), and disrupted by vortexing with glass beads. The cross-linked chromatin was pelleted by centrifugation at 200,000 g for 12 minutes, resuspended in 1 mL lysis buffer, and sonicated to yield DNA fragments of 300 base pairs average size. Soluble chromatin was separated from insoluble materials by centrifugation at 13,000 g for 15 minutes. Finally, the volume of soluble chromatin was adjusted to 10 mL with dilution buffer (16.7 mM Tris-HCl, pH 8.0, 16.7 mM NaCl, 1.2 mM EDTA, 0.01% SDS, 1.1% Triton-x100, 1 mM PMSF) and the resultant chromatin solution was stored in 1 mL aliquots at −80° C. For immunoprecipitation assays, 5 µL rabbit anti-Gal4p serum, 5 µL anti-Gal80p serum, or 5 µL anti-Gal3p serum was added to 1 mL chromatin solution. After overnight incubation on a rotator, 75 µL of protein-A-Sepharose beads were added, and the reactions were incubated for two more hours. Precipitated protein-DNA complexes were eluted from the beads, cross-linked reversed, treated with proteinase K, and analyzed by quantitative radioactive PCR using primer pairs GANG67/68 for the UAS$_{GAL}$ region and GANG71/72 for an intergenic control region located 5 kb downstream from the GAL1 gene. The sequences of the primers were GANG67: CATGGCATTAC-CACCATATACATATCC (SEQ ID NO:17); GANG68: GAAGGTTTGTGGGGCCAGGTTACTGC (SEQ ID NO:18); GANG71: GTGCATTTGGCCTTCAATGAGC (SEQ ID NO:19); GANG72: AAGTGATGTTCGACATAC-CTGTAAC (SEQ ID NO:20). A dilution (1/30,000) of input DNA, 1/200 of anti-Gal4p antibody precipitated DNA, 1/50 of anti-Gal80p antibody precipitated DNA, and 1/25 of anti-Gal3p antibody precipitated DNA were used as template for the various reactions. PCR conditions were as follows: 0.5 µM each primer, 0.25 mM each dNTP, 1.5 mM MgCl$_2$, 0.06 mCi/mL ($\alpha$-$^{32}$P)dATP in a 20 µL reaction volume. PCR cycle regimen was as follows: 3 minutes at 94° C., followed by 25 cycles of 1 minute at 94° C., 1 minute at 52° C., and 1 minute at 72° C. PCR products were resolved on 8% polyacrylamide gels in 1× TBE buffer. Quantitation of incorporated {$\alpha$-$^{32}$P}dATP in the PCR products was performed using a PhosphorImager (Molecular Dynamics) analysis.

Figure 3:
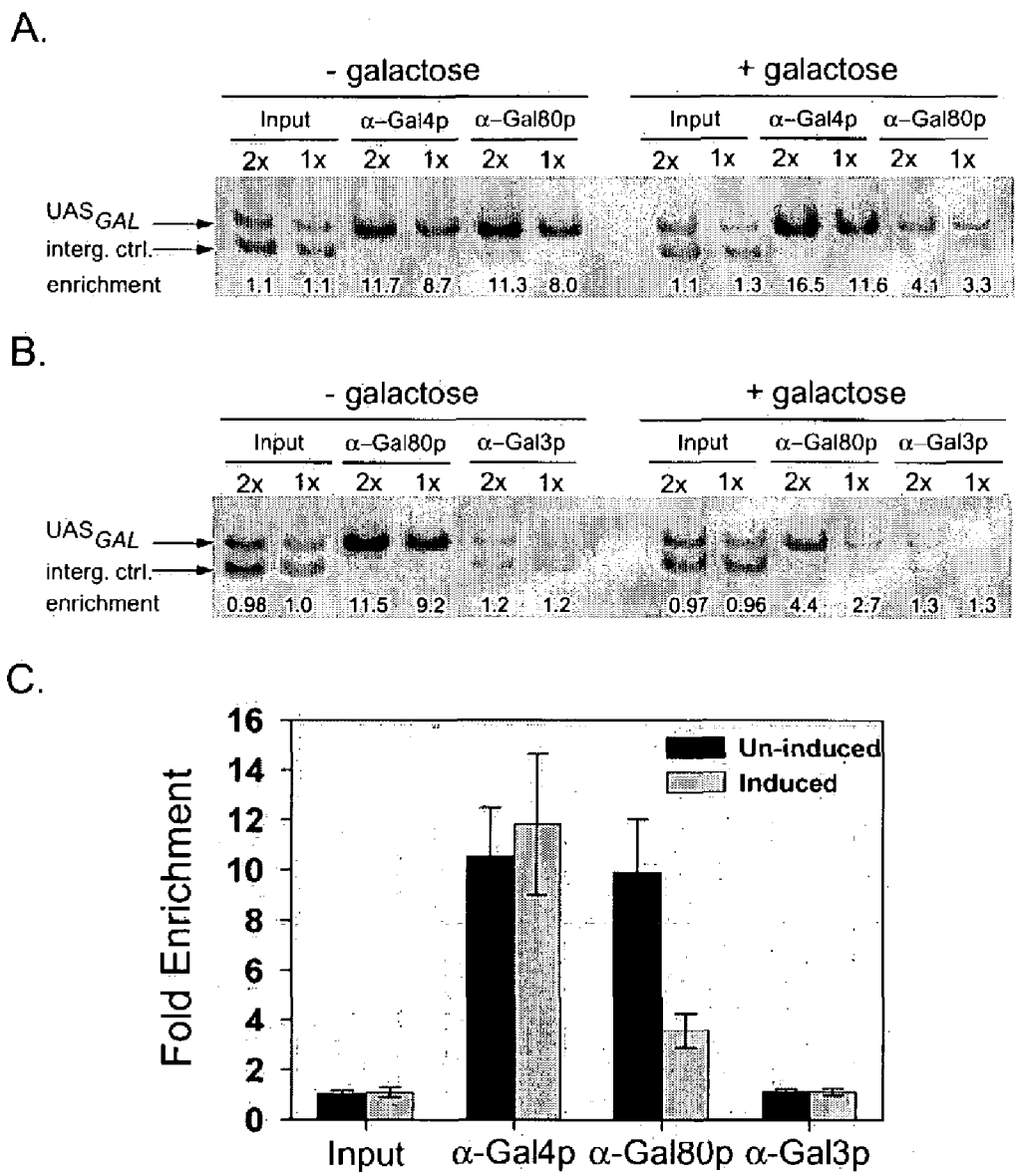
FIG. 3A through 3C. (Yeast cells) Analysis of the association of Gal4p, Gal80p and Gal3p with $UAS_{GAL}$ sequences using chromatin immunoprecipitation. These data establish that galactose triggers a reduction of the amount of Gal80p bound to Gal4p at the $UAS_{GAL}$ site within GAL gene promoters. When considered with the illustration in FIG. 1C, these data establish that interaction of Gal3p and Gal80p in the cytoplasm leads to a reduction of Gal80p bound to Gal4p in the nucleus within the GAL gene promoters. Yeast cells were grown to early-log phase in medium containing 2% glycerol/3% lactic acid/0.05% glucose (-galactose, un-induced) and induced with 2% galactose for 20 minutes (+galactose, induced). The 344 bp PCR product ($UAS_{GAL}$) corresponds to the region extending from −600 to −257 relative to the +1 of the GAL1 gene. The 287 bp PCR product (intergenic control) corresponds to an intergenic region located 5 Kb downstream from the GAL1 promoter and served as a control for background binding in the immunoprecipitation. The ratio between the 344 bp and 287 bp PCR products (fold enrichment) is calculated to normalize results and assess promoter occupancy.

Because Gal80p is associated with the UAS$_{GAL}$ solely through its binding to Gal4p, comparison of the amount of the UAS$_{GAL}$ DNA associated with Gal4p and Gal80p provided an assessment of the interaction between Gal4p and Gal80p. It was found that, while Gal4p occupancy of the UAS$_{GAL}$ site slightly increased upon galactose signaling, the Gal80p association with the UAS$_{GAL}$ region decreased significantly. Repeated trials did not yield any evidence that Gal3p is associated with the GAL 1/10 gene promoter (results shown in FIG. 3). These data indicated that concurrent with galactose-induced interaction between Gal3p and Gal80p in the cytoplasm, the association between Gal80p and UAS$_{GAL}$-bound Gal4p decreases in the nucleus. These results were contrary to a long-held view (Leuther & Johnston, 1992, "Non-dissociation of Gal4 and Gal80 in vivo after galactose induction," *Science* 256: 1333–1334) that Gal80 does not dissociate from Gal4 in response to galactose.

EXAMPLE 4

GAL Gene Expression Activated by Surrogate Protein-Protein Interactions in the Cytoplasm: The 80-Trap The results shown in Examples 1–3 above indicated that the galactose-triggered Gal3p-Gal80p interaction traps Gal80p in the cytoplasm, thereby causing the observed removal of Gal80p from the promoters of GAL genes and activation of Gal4p. The behavior of the Gal80p-Gal3p interaction in vivo is consistent with this view, as the membrane-bound Myr-Gal3p is shown to sequester Gal80p to the membranes where Myr-Gal3p is located (as shown in FIG. 1C).

Given the new insights into the activation of Gal4p shown here, a method for trapping Gal80p in the cytoplasm was developed for use as an assay to detect protein-protein interactions in the cytoplasm and/or nuclear export/localization sequences and to regulate Gal4p-activation of GAL gene promoters by small molecules other than galactose. In this method, termed the 80-Trap method, a specific bait protein (identified as a known protein of interest) is fused to Gal80p to create a fusion protein with Gal80 at either the amino- or carboxyl-terminus of Gal80p. The bait protein's binding partner, prey protein (either another known protein of interest or a multiplicity of yet unidentified potential partners encoded in a cDNA library), is tethered to the cell or mitochondrial outer membrane via fusion to membrane targeting sequences (myristoylation or mitochondrial Tom70 sequence, 10 respectively). If the bait and prey proteins interact in the cytoplasm, Gal80 is trapped in the cytoplasm and prevented from inhibiting Gal4p-mediated transcriptional activation of GAL gene promoters in the nucleus.

Using this method, it was expected that substituting Gal3p with a surrogate-binding factor for Gal80p in the cytoplasm would activate GAL gene expression. To test this possibility, the interaction between Fpr1p and Can1p that is elicited by a small membrane-permeable molecule FK506, a macrolide isolated from *Streptomyces tsukubaensis* (Kino et al., 1987, *J Antibiot* (Tokyo) 40: 1249–1255; Liu et al., 1991, *Cell* 66: 807–815; Cardenas et al., 1995, *Embo J* 14: 2772–2783, and Griffith et al., 1995, *Cell* 82: 507–522) was used. Expression constructs and production of yeast strain ScGP786 was as is described below.

pGP82 (Gal80-Fpr1) is made up of nucleotide sequences encoding a GAL80, 2 HA tags, and FPR1 on a pRS416 (Sikorski and Hieter, 1989, *Genetics* 122: 19–27) backbone. GAL80 sequence was obtained from yeast genomic clones using polymerase chain reaction, and having the sequence disclosed at, bin/SGD/locus.pl?locus=gal80. HA was derived from oligonucleotides GANG33/34. FPR1 was the ClaI digested PCR product generated by using yeast genomic DNA as template and GANG 117/118 as primers, pGP130(Myr-Hom3) contains an ADH2 promoter, CFP sequence, and HOM3 sequence on a pRS424 (Sikorski and Hieter, 1989, *Genetics* 122: 19–27) backbone. The ADH2 promoter was the PCR product using yeast genomic DNA as template and GANG83/84 as primers. CFP was the PCR product using pDH3 as template (Yeast Resource Center, University of Washington) and GANG101/112 as primers. HOM3 was a PCR product using yeast genomic DNA as template and GANG125/126 as amplification primers, pGP139 (Myr-Cna1) contains an ADH2 promoter, CFP sequence, and CNA1 sequence. An ADH2 promoter was obtained as a PCR product using yeast genomic DNA as template and GANG83/84 as primers. CFP was obtained as a PCR product using pDH3 as template (Yeast Resource Center, University of Washington) and GANG101/112 as primers. CNA1 was obtained from a PCR product using yeast genomic DNA as the template and GANG141/142 as primers.

ScGP786 was derived from Sc786 (Blank et al., 1997, *Mol. Cell. Biol.* 17: 2566–2575). For the replacement of FPR1 gene with ADE1, ADE1 ORF under control of a GAL1/10 gene promoter was cloned into plasmid pUG6 carrying the dominant Kan$^r$ gene (Guldener et al., 1996, *Nucleic Acids Research* 24: 2519–2524). Yeast cells were transformed by the PCR product from the reaction using oligonucleotide primers GANG119/120 with 45 bp homology to FPR1 chromosomal locus at 33 nt upstream and 33 nt downstream. Transformation and homologous recombination events were selected by plating cells on YPD plates containing 200mg/L Geneticin (G-418 sulphate).

Figure 4:
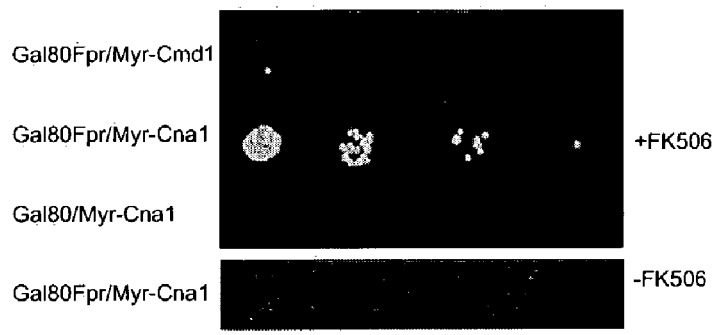
FIGS. 4A and 4B. (Yeast cells) Surrogate protein-protein interaction activates GAL gene expression.
Figure 4:
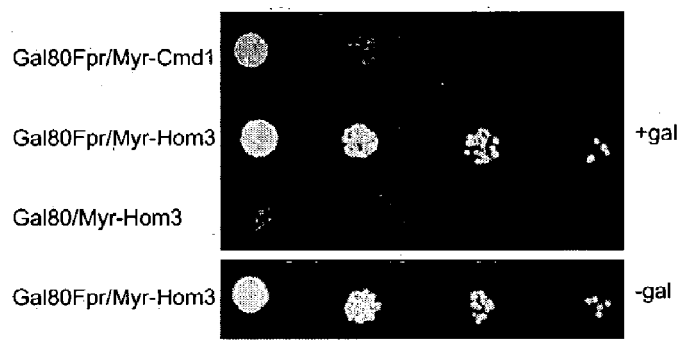

FK506 was used to trigger the interaction between a Gal80-Fpr1p fusion and plasma membrane-localized Myr-Can1p. It has been shown that FK506 by itself does not activate transcription of the GAL genes (Biggar and Crabtree 2001, *Embo. J.* 20:3167–3176). Induction of the galactose-inducible HIS3 reporter gene was assayed. Cells of a gal80Δ gal3Δ gal1Δ strain (ScGP786) carrying both Gal80-Fpr1 and Myr-Can1p plasmids exhibited evident growth only on the plate containing FK506 (shown in FIG. 4A). It has been reported that Fpr1p also interacts with Hom3p, the aspartokinase, in the absence of FK506 in a yeast two-hybrid assay (Alarcon and Heitman, 1997, *Mol. Cell Bio*., 17: 5968–5975). Following a scheme that paralleled the one above, it was found that the heterologous interaction between Gal80-Fpr1p and Myr-Hom3p was able to activate HIS3 reporter gene expression (shown in FIG. 4B). It was also determined by the Western analyses that the Gal80-Fpr1p fusion was present at a slightly higher level in cells containing both Gal80-Fpr1p and Myr-Hom3p as compared to cells harboring the non-interacting controls, Gal80-Fpr1p and Myr-Cmd1 p, indicating that activation of the HIS3 reporter gene was not due to the degradation of Gal80-Fpr1p in cells expressing Myr-Hom3p.

The above results demonstrated that Gal4p-mediated gene expression may be activated by the cytoplasmic interaction of surrogate proteins. Thus, the potential interaction between proteins of interest and uncharacterized cDNAs may be detected with this novel cytoplasmic based system. In addition to the 'forward' two-hybrid modes described above, the system may also be used effectively in the 'reverse' two-hybrid mode (analogous to the use of the conventional two hybrid system as shown in Vidal et al., 1996, *Proc. Natl. Acad. Sci. USA* 93:10315–20). The 80-Trap system may select for loss of interaction mutations in either cDNA (bait or prey) and provides a method for identifying and mapping the amino acids involved in protein-protein interaction.

EXAMPLE 5

Figure 5:
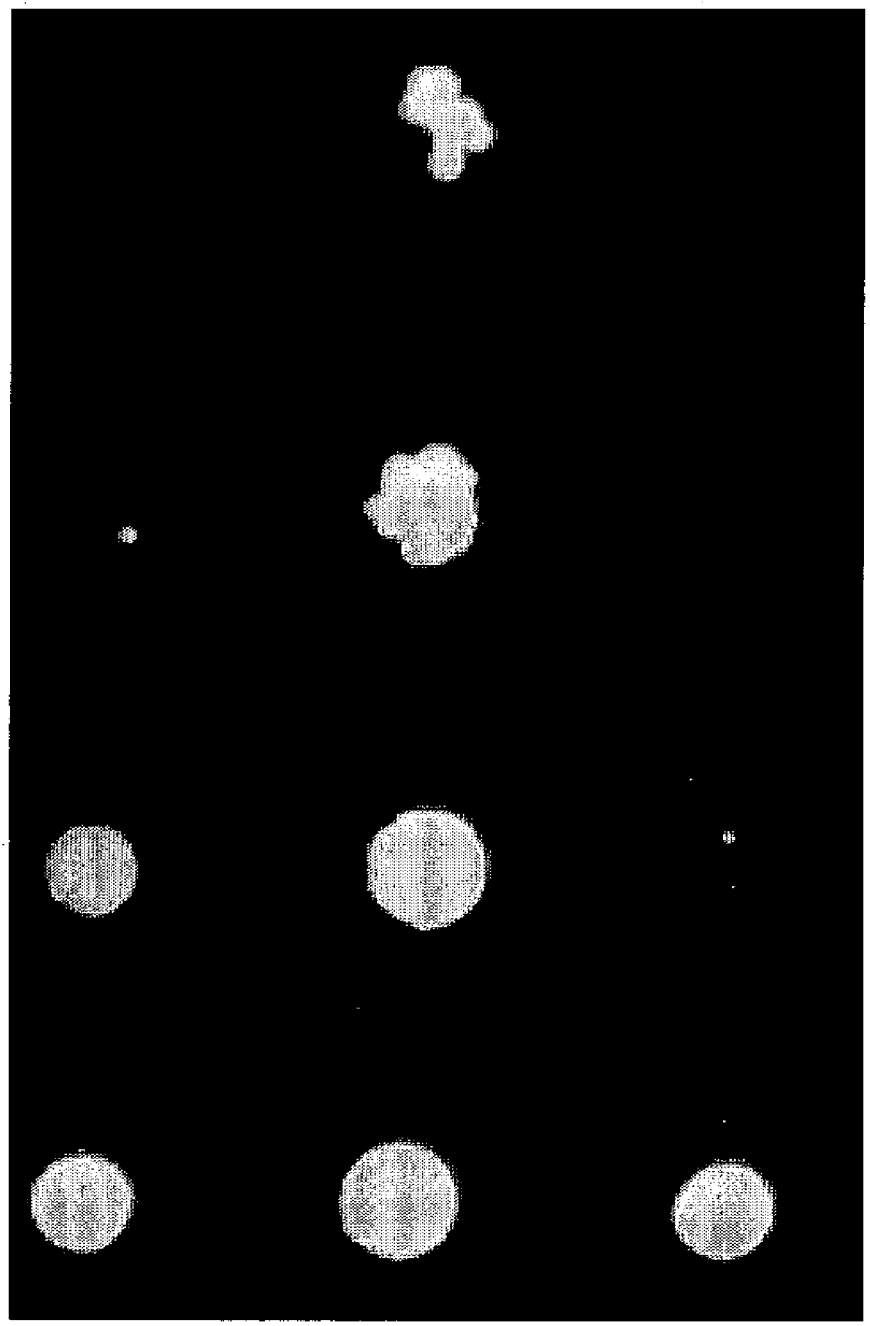
FIG. 5. (Yeast cells) A membrane-targeted transcription factor activates GAL gene expression through interaction with Gal80-TBP. Galactose-independent HIS3 reporter (expression as a result of Gal80-TBP and Myr-TAF145 interaction; lane 1). Lane 2 illustrates the positive control: interaction between two proteins known to interact: Fpr1 (in fusion with Gal80) and Hom3 (fused to the Myr sequence and CFP). Lane 3 is the negative control with Gal80-TBP tested against just the Myr sequence. The nutrient agar plate used here contained 3% glycerol/2% lactic acid as carbon source and lacked histidine, tryptophan and uracil.

Detecting Transcriptional Proteins Interactions in Yeast With The 80-Trap Method In conventional yeast two-hybrid methods, transcriptional activator proteins can activate two-hybrid reporters through either direct binding to the RNA polymerase or through binding to other proteins that in turn bind to an RNA polymerase subunit. The protein interactions for the 80-Trap occur in the cytoplasm and would thus circumvent the false activation of GAL promoters. To examine the actions of transcriptional proteins in the 80-Trap system, the transcriptional protein, TATA binding protein (TBP), was fused to Gal80p. The N-terminal domain (amino acids 1–71) of TAF145 was fused to the myristoylation sequence. TAF145 and TBP are established components of the transcriptional machinery and are known to interact via protein-protein interactions (Kokubo, et al., 1998, *Mol. Cell. Biol.* 189: 1003–1012). Heterologous interaction between the Gal80-TBP and Myr-TAF145 was able to activate the HIS3 reporter gene expression (shown in FIG. 5, line 1).

Figure 6:
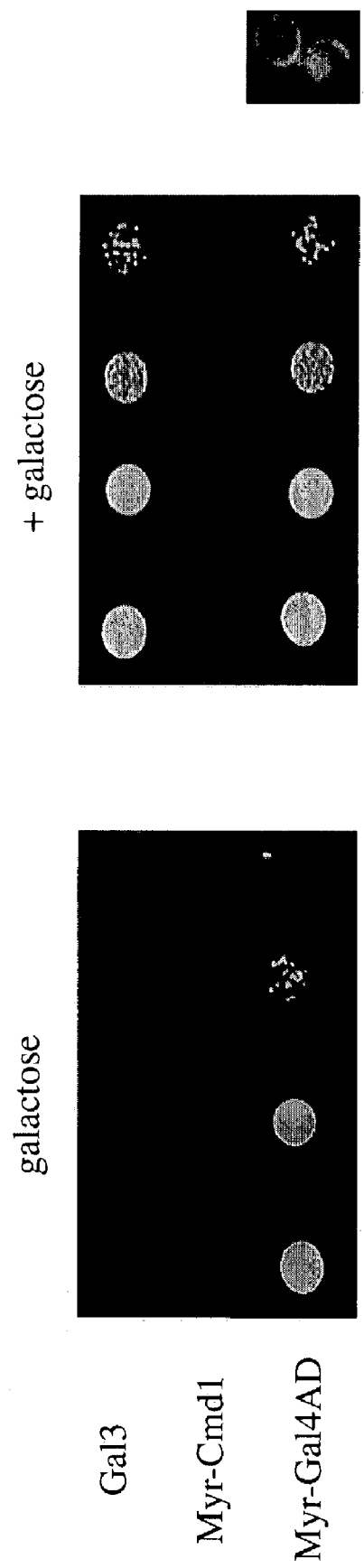
FIG. 6. (Yeast cells) Membrane targeted transcriptional activation domain of Gal4p (Gal4AD; amino acid 758–881) activates HIS3 reporter gene expression. A yeast strain harboring a $UAS_{GAL}$-HIS3 reporter was transformed with Myr-Gal4AD. The photomicrograph on the right shows the membrane localization of Myr-Gal4AD in yeast cells. Transformed cells were spotted on synthetic medium plates lacking histidine, tryptophan and uracil and containing 3% glycerol/2% lactic acid as carbon source. Cells showed evident growth in the absence of galactose, indicating an interaction between membrane-localized Gal4AD and Gal80p caused activation of the HIS3 reporter gene. As controls, cells carrying Gal3p exhibited growth only in the presence of galactose.

In a subsequent study, the transcription activation domain (AD) of Gal4p was tethered to the cell membrane by fusion to the myristoylation signal. Cells harboring the Myr-Gal4 (AD) fusion deplete GAL80p from the nucleus and in turn permitted the native Gal4p to activate transcription of GAL reporter genes (as shown in FIG. 6). Similarly, tethering of any one of a multiplicity of other transcription activation domains outside of the nucleus and its interaction with a binding partner fused to Gal80p would result in reporter gene activation.

These results demonstrated that transcription factors, and transcription activator domains may be tethered to the cells plasma and vesicular membranes or mitochondrial outer membrane and used to accurately screen for potential protein-protein interactions. This method permits the study of protein interactions not suitable for conventional two-hybrid approach. Because protein interactions occur in the cytoplasm, the potential for false activation of reporter genes is reduced, and the potential for detecting protein interactions when one or both of the proteins require a cytoplasmic location is optimized.

TABLE 2

Oligonucleotide Primers

| | | |
|---|---|---|
| GANG33 | (SEQ ID NO:21) | CGT TAC CCA TAC GAC GTC CCA GAC TAC GCT GGT TGG |
| GANG34 | (SEQ ID NO:22) | CGC AAC CA GCG TAG TCT GGG ACG TCG TAT GGG TAA |
| GANG83 | (SEQ ID NO:23) | GAT ACT TCC CAA TTC GTC TTC AGA G |
| GANG84 | (SEQ ID NO:24) | CTG GAA TAG ACT AGT TGT GTA TTA CGA TAT AG |
| GANG101 | (SEQ ID NO:25) | CCA ATG CAT GTA TGA GTA AAG GAG AAG AAC TTT TCA C |
| GANG113 | (SEQ ID NO:35) | AAA AAA GTA CAg cat gca aAT GTC CTC CAA TCT TAC CGA AG |
| GANG114 | (SEQ ID NO:36) | GAT GCA CCT Aat cga ttT TTA GAT AAC AAA GCA GCG AAT TG |
| GANG112 | (SEQ ID NO:26) | TTT GTA TTg CAT gcg gat cGG GGA TC |
| GANG117 | (SEQ ID NO:27) | ACA AGT AAT Aat cga tcg TCT GAA GTA ATT GAA GGT AAC |
| GANG118 | (SEQ ID NO:28) | TTT GCT TTT Aat cga ttG TTG ACC TTC AAC AAT TC |
| GANG119 | (SEQ ID NO:29) | ATA AAC TCG TGA AAG CTT AAA GTA AGG CCT TTC ACC TAA ACT CGA GTC GTT AGA ACG CGG CTA C |
| GANG120 | (SEQ ID NO:30) | TCA ATT AAG GCT CAG ATA CTT ACC ATA AAC ATA AAT AAA AAG CAG TCA CTA TAG GGA GAC CGG CAG |
| GANG125 | (SEQ ID NO:31) | TTT AAC TTT TAC gca tgc aaA TGC CAA TGG ATT TCC AAC CTA C |

TABLE 2-continued

Oligonucleotide Primers

GANG126 (SEQ ID NO:32)  GGT GGA TTT Agg cgc ctA ATT CCA AGT CTT
                        TTC AAT TGT TC GANG141 (SEQ ID NO:33)  CAA CGC CAg cAT Gct gTC GAA AGA CTT GAA
                        TTC TTC ACG C GANG142 (SEQ ID NO:34)  GTG CTT AGa tcg att aCG TTT CAT TCA AAC CTT
                        CAG TCC C

EXAMPLE 6

Figure 7:
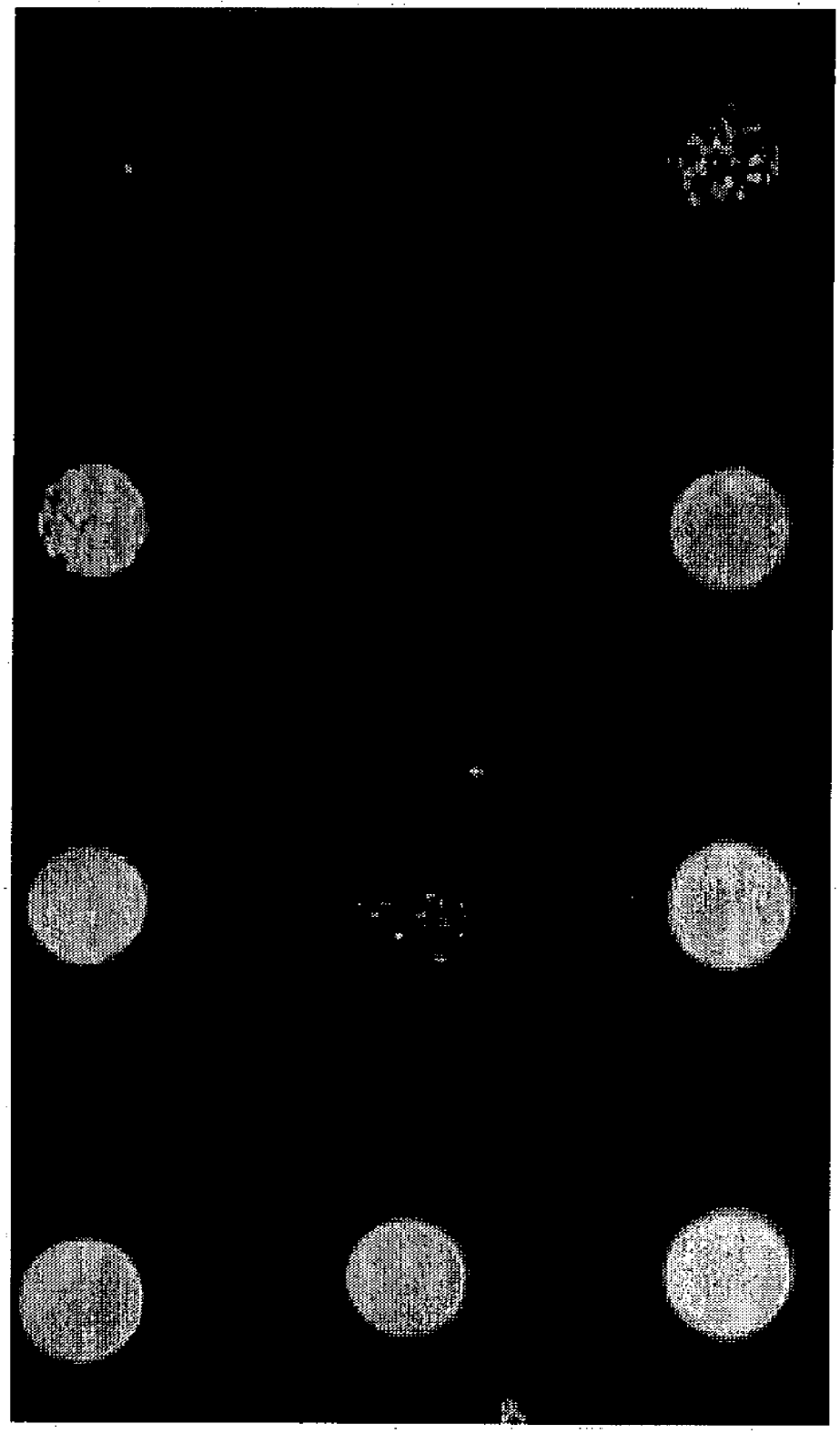
FIG. 7. (Yeast cells) Addition of exogenous nuclear export sequence (NES) to Gal80p causes increased Gal4p-mediated reporter gene activation. Fusion of an NES to Gal80p increases Gal4p activation of a reporter gene in response to low levels of galactose. Top row, $P_{Gal80}$-Gal80-NES. 2. Middle row, $P_{Gal80}$-Gal80. 3. Bottom row, Gal80-deletion. The host yeast strain: Sc725 (ura3⁻, trp1⁻, his3⁻, gal80Δ). Growth of yeast on agar lacking uracil and histidine and containing 10 mM 3-Azotriazole (to eliminate leaky HIS3 expression) and carbon sources 3% glycerol, 2%lactic acid, 0.02% glucose and 0.1% galactose. Photo taken 7 days after spotting.

Detection of Nuclear Export Sequences and Nuclear Localization Sequences in Yeast by Fusion to Gal80p In addition to measuring protein-protein interactions, the methods of the present invention are useful for detecting peptides containing nuclear export or nuclear localization sequences. For detecting nuclear export sequences, Gal80p is fused to a cDNA or one or a plurality of members of a cDNA library. cDNAs encoding peptides containing a nuclear export sequence (NES) sequester Gal80p to the cytoplasm. This in turn permits Gal4p-mediated transcriptional activation of GAL gene promoters in the presence of 0.01% galactose, a level normally not sufficient to permit Gal4p-mediated transcriptional activation of GAL gene promoters. (shown in FIG. 7).

For detecting nuclear localization sequences, cDNAs encoding proteins containing an NLS sequence are fused to Gal80p. The presence of an exogenous nuclear localization sequence in said protein results in sequestration of Gal80p in the nucleus and prohibits export of Gal80p to the cytoplasm, resulting in the inability to bind to Gal3p in the cytoplasm when galactose is present. This inability of Gal80p to exit from the nucleus and bind to Gal3p allows Gal80p to maintain its high concentration in the nucleus and binding to Gal4p and prevents Gal4p-mediated activation of genes whose expression is regulated by galactose and Gal4p. In yeast cells harboring a Ura3 gene expressed from a GAL gene promoter, said fusion of an NLS sequence to Gal80p prevents the URA3 enzyme from being produced and consequently protects the cell from the toxic effects of 5-FOA. The yeast cells harboring said NLS-Gal80p fusion thus grow as colonies on nutrient agar containing 3% glycerol/2% lactic acid, 0.1% galactose as carbon source and 5-FOA . In summary, the methods of the present invention provide a means for detecting both nuclear export and nuclear localization sequences.

EXAMPLE 7

Construction of Plasmid Expressing GFP Fusion Proteins for Experiments in Cells from Multicellular Organisms A full-length 1559-bp yeast GAL3 ORF from pTEB16 (Blank et. al., *Mol Cell Biol.* 1997) was PCR-amplified with Pfu DNA polymerase (Invitrogen) and primers VP0001 and VP0005 that created Sac II and BamHI sites upstream and downstream of the GAL3 ORF accordingly. The GAL80 ORF sequence was amplified from pGP15A (Peng, G. and Hopper, J. E., Mol Cell Biol, 2000) using primers VP0003, VP0006 that created Sac II, BamHI restriction sites flanking the GAL80 ORF sequence. The recipient plasmid was pEGFP-NI from (CLONTECH Laboratories, Inc) which contains the enhanced GFP ORF sequence expressed from the CMV immediate early promoter and transcriptionally terminated by the SV 40 early mRNA polyadenylation signal. Amplified GAL3 and GAL80 sequence were inserted to the pEGFP-NI plasmid that had been digested with SacII and BamHI. The resulting plasmids pVRP2 and pVRP4 had GFP fused to the COOH terminus of GAL3 and GAL80, respectively.

Primers:

VP0001-  5' AATACCGCGGATGAATACAAACGTTCCA 3'
         (SEQ ID NO:4),

VP0005-  5' AATAGGATCCGCTTGTTCGTACAAACAAGT 3'
         (SEQ ID NO:5),

VP0003-  5' AATACCGCGGATGGACTACAACAAGAGA 3'
         (SEQ ID NO:37),

VP0006-  5' AATAGGATCCGCTAAACTATAATGCGAGAT 3'
         (SEQ ID NO:38).

Cell Culture, Transfection and Microscopy for Experiments in Cells from Multicellular Organisms HEK 293 and 3T3 cells were cultured at 37° C. in 5% $CO_2$ atmosphere in Dulbecco's modified Eagle's medium (DMEM) supplemented with 10% (v/v) fetal calf serum (Sigma) containing penicillin and streptomycin. As 3T3 cells required the additional supplement of glutamine. Transfections were carried out using the lipofectAMINE™ 2000 REAGENT (Invitrogen Life technologies). Plasmid DNA (8 □g) and 15 □l of lipofectamine were added to cells on 35 mm culture dishes according to the manufacturer's instructions. Typically, HEK 293 and 3T3 cells at 60±70% confluency in medium containing 2 ml of complete DMEM were transfected as above. This routinely resulted in 20–40% transfection efficiency, as determined by visualization of expressed GFP by fluorescence microscopy of live cells 24 h after transfection. For live cell microscopy the cells were grown on glass cover slips in 35 mm plates.

Figure 8:
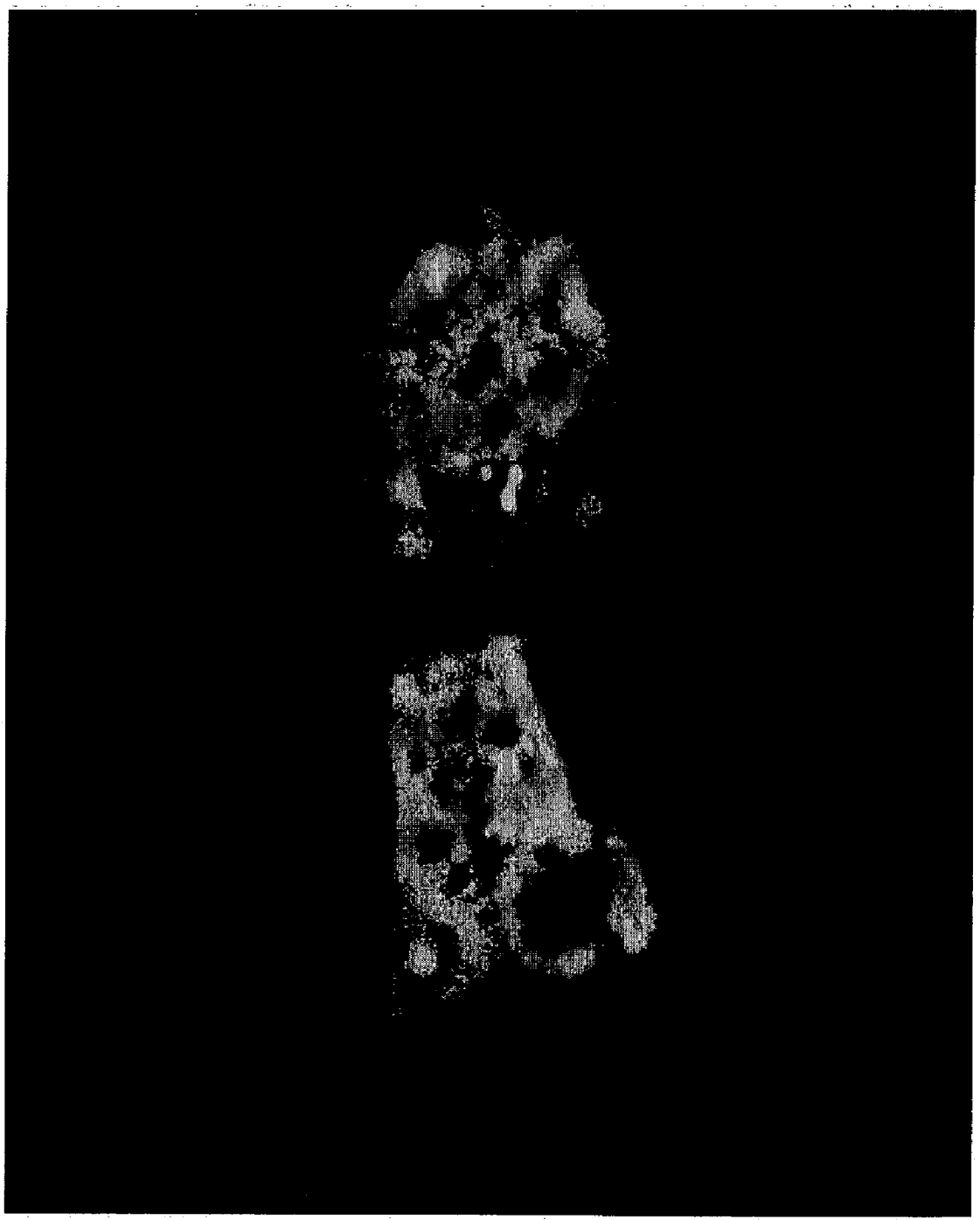
FIG. 8. (Multicellular organisms or cells therefrom) Gal80GFP in cells from a multicellular organism (mouse 3T3). Note that Gal80GFP is in both the nucleus and the cytosol, but is excluded from the nucleoli. Also note size of nuclei is same as in case of FIG. 9 where perimeter of nuclei is more defined due to exclusion of fluorescent Gal3GFP. Imaging was performed with an Olympus Confocal Scanning Microscope using a 100× objective.
Figure 9:
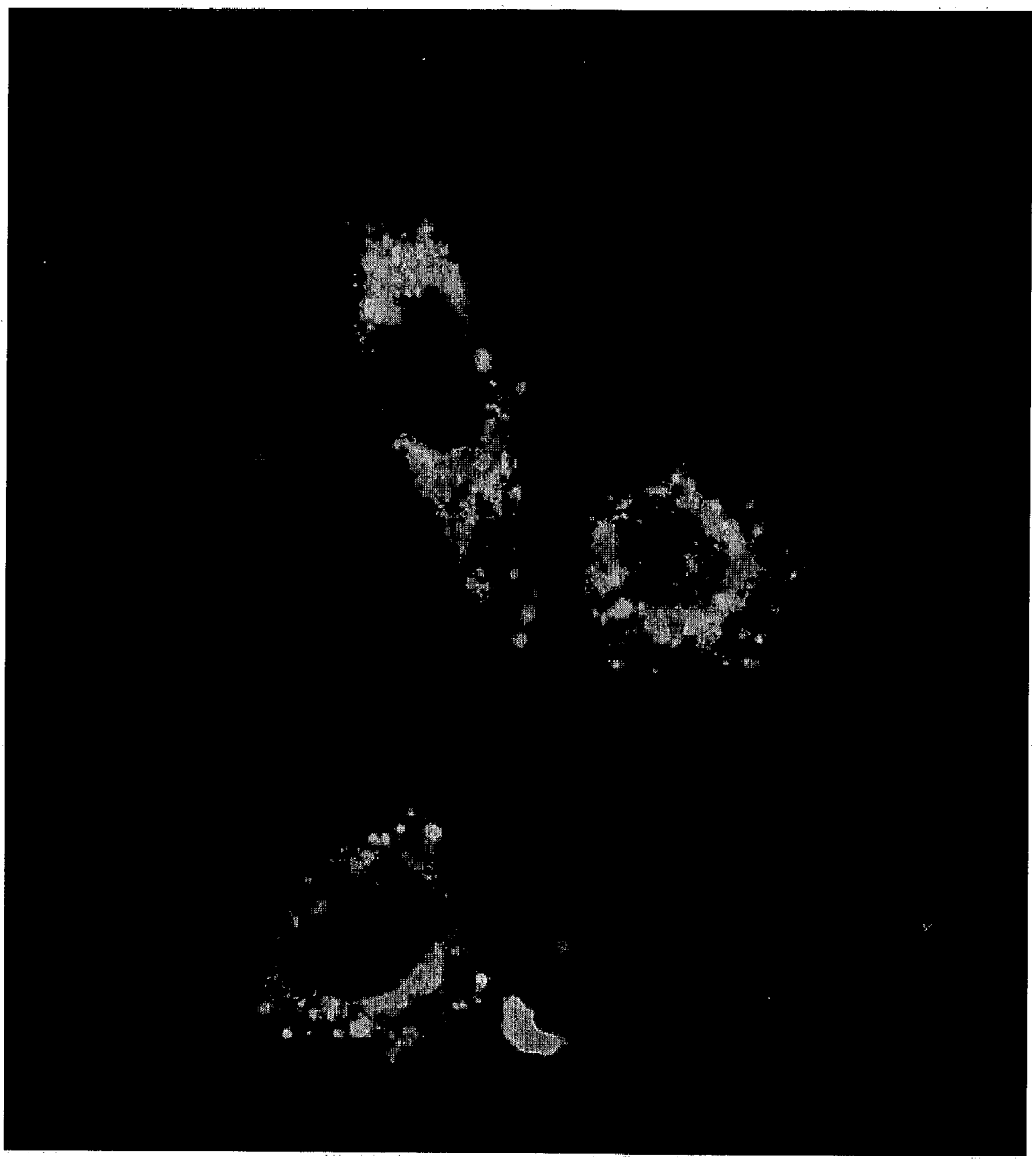
FIG. 9. (Multicellular organisms or cells therefrom) Gal3GFP in cells from a multicellular organism (mouse 3T3). Note that the nuclei are devoid of Gal3GFP. Imaging was performed with an Olympus Confocal Scanning Microscope using a 100× objective.

Fluorescence Imaging Gal3-GFP and Gal80-GFP Fusion Proteins in Multicellular Organisms or Cells Therefrom For imaging GFP-fusion proteins in fixed cells the protocol of Dundr, M., et al., (2000 J Cell Biol 150 p433446) was used. After transfection of cells with plasmid expressing the GFP fusion protein of interest, the cells were seeded on sterile cover slips and grown typically 16–24 hours. The cells were fixed cells in 2% formaldehyde in PBS, pH 7.4 for 15 min. at room temperature directly on the cover slip, quickly rinsed in 4 ml PBS, pH 7.4 and washed in 2 ml PBS, pH 7.4, 2×5 min. at room temperature. The cover slip containing the fixed cells was positioned face down onto a 10 □l drop of mounting media on a glass slide. Imaging was performed with an Olympus Confocal Scanning Microscope using a 100× objective. The evidence shows that i) the Gal80p protein exists in both the nucleus and the cytoplasm (FIG. 8), and ii) the Gal3 protein is located only in the cytoplasm, i.e., excluded from the nucleus (FIG. 9).

It should be understood that the foregoing disclosure emphasizes certain specific embodiments of the invention and that all modifications or alternatives equivalent thereto are within the spirit and scope of the invention as set forth in the appended claims.

---

We claim:

1. A method for detecting protein-protein interactions in a host cell cytoplasm, the method comprising:
   a. introducing a first recombinant expression construct encoding a first protein or protein-binding fragment thereof fused with the amino- or carboxyl-terminus of a transcriptional inhibitor;
   b. introducing a second recombinant expression construct encoding a second protein or protein-binding fragment thereof fused to a cytoplasm localization sequence,
   wherein the first or second protein or both is a protein encoded by a cDNA molecule or a member of a cDNA library, wherein said library comprises a plurality of fusion proteins in which the transcription inhibitor protein is fused to each of a plurality of members of said cDNA library in each species of fusion protein comprising said plurality of fusion proteins,
   wherein upon interaction of the first and second proteins in the cell cytoplasm, said transcriptional inhibitor is localized to the cytoplasm, wherein transcription of a gene operably linked to a promoter that is sensitive to or regulated by said transcriptional inhibitor is increased; and
   c. detecting said increased transcription of said gene, wherein said protein-protein interaction is detected thereby.

2. The method of claim 1, wherein the cytoplasm localization sequence is a membrane targeting sequence.

3. The method of claim 2, wherein the membrane targeting sequences are a myristoylation sequence, mitochondrial outer membrane targeting sequence, or a membrane anchoring sequence.

4. The method of claim 3 wherein the myristoylation sequence is MGCTVSTQTIGDESDP (SEQ ID NO:1).

5. The method of claim 3 wherein the mitochondrial outer membrane targeting sequence is the N-terminal sequence of Tom70/Mas70 protein, MKSFITRNKTAILATVAATGTAIGAYYYY (SEQ ID NO: 3).

6. The method of claim 1, wherein the second protein is a transcriptional activator protein or one of a multiplicity of proteins that participate in protein-protein interactions to bring about transcriptional activation.

7. The method of claim 1, wherein the second protein is a transcriptional activator protein or one of a multiplicity of proteins that participate in protein-protein interactions to bring about transcriptional activation.

8. The method of claim 1, wherein said first or second proteins are detectable or produce detectable metabolites.

9. The method of claim 1, wherein the gene expressed from the promoter that is sensitive to or regulated by the transcriptional inhibitor is one of a multiplicity of genes that encode detectable proteins.

10. The method of claim 1, wherein the gene operably linked to a promoter that is sensitive to or regulated by said transcriptional inhibitor is a gene expressed from a promoter that can be activated by GAL4 protein.

11. The method of claim 10, wherein the gene expressed from the promoter that can be activated by GAL4 protein is one of a multiplicity of genes that encode detectable proteins.

12. The method of claim 10, wherein the promoter that can be activated by GAL4 protein is one of a multiplicity of promoters that contain a $UAS_{GAL}$ site.

13. The method of claim 10, wherein the gene operably linked to a promoter that is sensitive to or regulated by said transcriptional inhibitor is one of a multiplicity of genes encoding a detectable product.

14. The method of claim 10, wherein the transcription inhibitor is Gal80p.

15. The method of claim 1, wherein the gene operably linked to a promoter that is sensitive to or regulated by said transcriptional inhibitor is a selectable gene, wherein increased expression of said gene confers a growth advantage on the cell or distinguishes the cell in some detectable manner.

16. The method of claim 14, further comprising:
   d. subjecting the host cell to selective growth conditions; and
   e. detecting increased growth or survival of said cells under selective growth conditions; wherein said protein-protein interaction is detected thereby.

17. A method for isolating said first or second fusion proteins according to claim 1, the method comprising:
   a. detecting increased expression of the gene operably linked to a promoter that is sensitive to or regulated by said transcriptional inhibitor; and
   b. isolating said first or second fusion proteins.

18. A method for detecting protein-protein interactions in the cytoplasm of a cell of a multicellular organism, the method comprising:
   a. introducing a first recombinant expression construct encoding a first protein or protein-binding fragment thereof fused with the amino- or carboxyl-terminus of Gal80p;
   b. introducing a second recombinant expression construct encoding a second protein or protein-binding fragment thereof fused to a cytoplasm localization sequence, wherein upon interaction of the first and second proteins in the cell cytoplasm, said Gal80p is localized to the cytoplasm, wherein transcription of a gene operably linked to a promoter that is sensitive to or regulated by said Gal80p is increased; and
   c. detecting said increased transcription of said gene, wherein said protein-protein interaction is detected thereby.

* * * * *

UNITED STATES PATENT AND TRADEMARK OFFICE
CERTIFICATE OF CORRECTION

| | |
|---|---|
| PATENT NO. | : 7,229,766 B2 |
| APPLICATION NO. | : 10/600389 |
| DATED | : June 12, 2007 |
| INVENTOR(S) | : Pilauri et al. |

Page 1 of 1

It is certified that error appears in the above-identified patent and that said Letters Patent is hereby corrected as shown below:

In Column 1, line 9 insert -- This application was made with government support under RO1 GM27925 awarded by The National Institutes of Health. The government has certain rights in the invention. --

Signed and Sealed this

Sixteenth Day of September, 2008

JON W. DUDAS
*Director of the United States Patent and Trademark Office*